United States Patent
De Jong et al.

(10) Patent No.: US 10,829,748 B2
(45) Date of Patent: Nov. 10, 2020

(54) MUTANT LIPASE AND USE THEREOF

(71) Applicant: DSM IP Assets B.V., Heerlen (NL)

(72) Inventors: Rene Marcel De Jong, Echt (NL); Willem Bijleveld, Echt (NL); Evert Tjeerd Van Rij, Echt (NL)

(73) Assignee: DSM IP ASSETS B.V., Heerlen (NL)

( * ) Notice: Subject to any disclaimer, the term of this patent is extended or adjusted under 35 U.S.C. 154(b) by 45 days.

(21) Appl. No.: 16/305,348

(22) PCT Filed: Jun. 8, 2017

(86) PCT No.: PCT/EP2017/063919
§ 371 (c)(1),
(2) Date: Nov. 28, 2018

(87) PCT Pub. No.: WO2017/211930
PCT Pub. Date: Dec. 14, 2017

(65) Prior Publication Data
US 2019/0185830 A1 Jun. 20, 2019

(30) Foreign Application Priority Data
Jun. 10, 2016 (EP) .................... 16173955

(51) Int. Cl.
*C12N 9/20* (2006.01)
*C12N 1/20* (2006.01)
(Continued)

(52) U.S. Cl.
CPC ............ *C12N 9/20* (2013.01); *A23C 13/16* (2013.01); *A23C 15/123* (2013.01);
(Continued)

(58) Field of Classification Search
None
See application file for complete search history.

(56) References Cited

U.S. PATENT DOCUMENTS

2006/0188625 A1  8/2006  Kortes
2010/0183767 A1  7/2010  Noordam
(Continued)

FOREIGN PATENT DOCUMENTS

EP     1130100 A1  9/2001
WO  2015087833 A1  6/2015

OTHER PUBLICATIONS

PIR Accession No. S41091, published Mar. 19, 1997 (Year: 1997).*
(Continued)

*Primary Examiner* — Richard C Ekstrom
(74) *Attorney, Agent, or Firm* — McBee Moore & Vanik IP, LLC

(57) ABSTRACT

The present invention relates to a polypeptide having lipase activity wherein the polypeptide, which, when aligned with a polypeptide according to SEQ ID NO: 1, comprises at least one amino acid substitution resulting in Ser (S), Ala (A) or Leu (L) at position 246, Trp (W) at position 307, Leu (L) at position 345, Ile (I) at position 365, and/or Phe (F) at position 534, wherein the position is defined with reference to SEQ ID NO: 1, wherein Ala(A) at position 1 in SEQ ID NO: 1 is counted as number 1 and a method for preparing the polypeptide.
The present invention further relates to a process for preparing a food product wherein a polypeptide according to the present invention is used.

21 Claims, 1 Drawing Sheet
Specification includes a Sequence Listing.

(51) Int. Cl.
*C12N 1/14* (2006.01)
*C12N 15/52* (2006.01)
*C12N 15/63* (2006.01)
*A23C 13/16* (2006.01)
*A23C 15/12* (2006.01)
*A23C 19/06* (2006.01)
*A23C 19/082* (2006.01)

(52) U.S. Cl.
CPC .......... *A23C 19/063* (2013.01); *A23C 19/082* (2013.01); *C12N 1/14* (2013.01); *C12N 1/20* (2013.01); *C12N 15/52* (2013.01); *C12N 15/63* (2013.01); *C12Y 301/01003* (2013.01)

(56) References Cited

U.S. PATENT DOCUMENTS

| | | |
|---|---|---|
| 2012/0288587 A1 | 11/2012 | Cheng |
| 2014/0099402 A1 | 4/2014 | Noordam |
| 2016/0319259 A1* | 11/2016 | Ishigaki ......... C12Y 301/01003 |
| 2019/0185830 A1* | 6/2019 | De Jong ................ C12N 9/20 |

OTHER PUBLICATIONS

PIR Accession No. S70849, published Oct. 28, 1996 (Year: 1996).*
PIR Accession No. A34329, published Jun. 22, 1990 (Year: 1990).*
PIR Accession No. A29923, published Dec. 8, 1988 (Year: 1988).*
Geneseq Accession No. BBA64811, published Jan. 30, 2014 (Year: 2014).*
International Search Report issue in counterpart Application No. PCT/EP2017/063919, dated Sep. 19, 2017.
Jutta Schmitt et al: "Blocking the tunnel: engineering of Candida rugosa lipase mutants with short chain length specificity", Protein Engineering, Oxford University Press, Surrey, GB, vol. 15, No. 7, (Jul. 1, 2002) pp. 595-601.
Database UniProt [Online] (Jan. 11, 2011), XP002763811, retrieved from EBI accession No. Uni Prot: E3RTT7 Database accession No. E3RTT7 sequence.
Database UniProt [Online] (Oct. 14, 2015), XP002763812, retrieved from EBI accession No. UniProt:AOAOJ9X5E4 Database accession No. AOAOJ9X5E4.

* cited by examiner

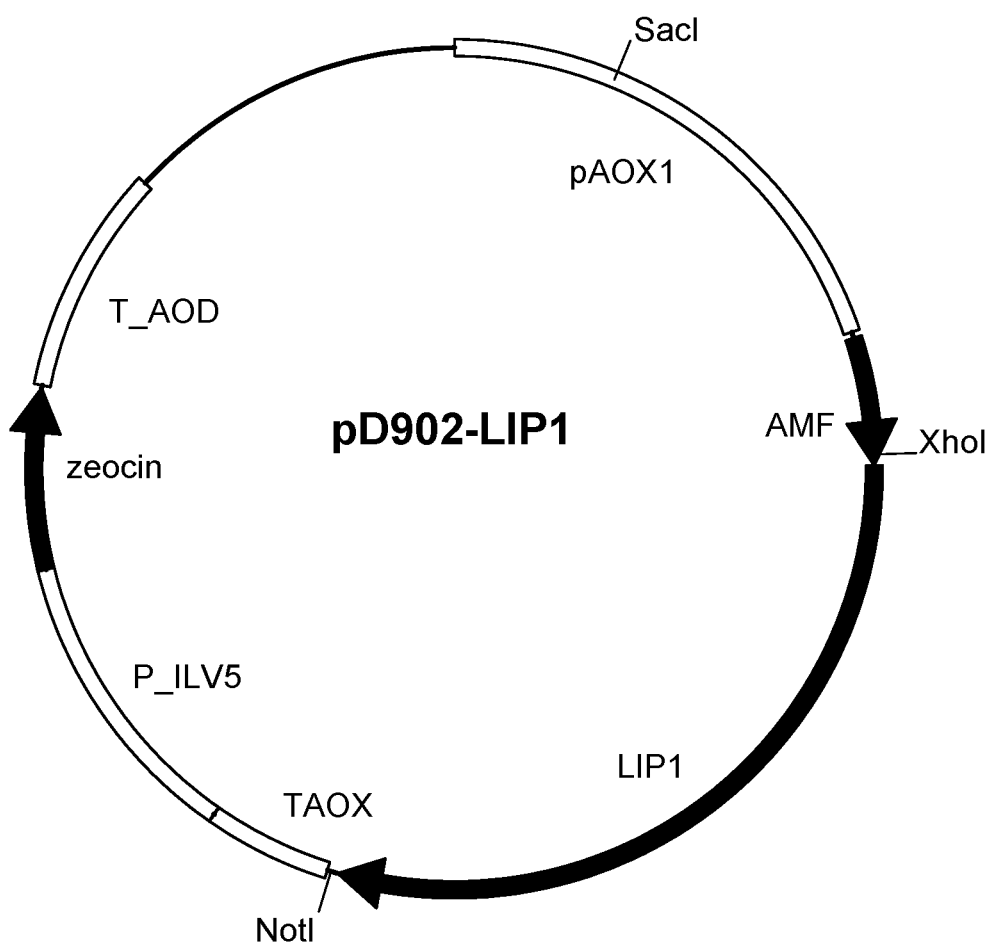

SEQUENCE LISTING

```
<160> NUMBER OF SEQ ID NOS: 7

<210> SEQ ID NO 1
<211> LENGTH: 534
<212> TYPE: PRT
<213> ORGANISM: Candida rugosa

<400> SEQUENCE: 1

Ala Pro Thr Ala Thr Leu Ala Asn Gly Asp Thr Ile Thr Gly Leu Asn
1               5                   10                  15

Ala Ile Ile Asn Glu Ala Phe Leu Gly Ile Pro Phe Ala Glu Pro Pro
            20                  25                  30

Val Gly Asn Leu Arg Phe Lys Asp Pro Val Pro Tyr Ser Gly Ser Leu
        35                  40                  45

Asp Gly Gln Lys Phe Thr Ser Tyr Gly Pro Ser Cys Met Gln Gln Asn
    50                  55                  60

Pro Glu Gly Thr Tyr Glu Glu Asn Leu Pro Lys Ala Ala Leu Asp Leu
65                  70                  75                  80

Val Met Gln Ser Lys Val Phe Glu Ala Val Ser Pro Ser Ser Glu Asp
                85                  90                  95

Cys Leu Thr Ile Asn Val Val Arg Pro Pro Gly Thr Lys Ala Gly Ala
            100                 105                 110

Asn Leu Pro Val Met Leu Trp Ile Phe Gly Gly Gly Phe Glu Val Gly
        115                 120                 125

Gly Thr Ser Thr Phe Pro Pro Ala Gln Met Ile Thr Lys Ser Ile Ala
    130                 135                 140

Met Gly Lys Pro Ile Ile His Val Ser Val Asn Tyr Arg Val Ser Ser
145                 150                 155                 160

Trp Gly Phe Leu Ala Gly Asp Glu Ile Lys Ala Glu Gly Ser Ala Asn
                165                 170                 175

Ala Gly Leu Lys Asp Gln Arg Leu Gly Met Gln Trp Val Ala Asp Asn
            180                 185                 190

Ile Ala Ala Phe Gly Gly Asp Pro Thr Lys Val Thr Ile Phe Gly Glu
        195                 200                 205

Ser Ala Gly Ser Met Ser Val Met Cys His Ile Leu Trp Asn Asp Gly
    210                 215                 220

Asp Asn Thr Tyr Lys Gly Lys Pro Leu Phe Arg Ala Gly Ile Met Gln
225                 230                 235                 240

Ser Gly Ala Met Val Pro Ser Asp Ala Val Asp Gly Ile Tyr Gly Asn
```

```
                        245                 250                 255
Glu Ile Phe Asp Leu Leu Ala Ser Asn Ala Gly Cys Gly Ser Ala Ser
                260                 265                 270

Asp Lys Leu Ala Cys Leu Arg Gly Val Ser Ser Asp Thr Leu Glu Asp
            275                 280                 285

Ala Thr Asn Asn Thr Pro Gly Phe Leu Ala Tyr Ser Ser Leu Arg Leu
        290                 295                 300

Ser Tyr Leu Pro Arg Pro Asp Gly Val Asn Ile Thr Asp Asp Met Tyr
305                 310                 315                 320

Ala Leu Val Arg Glu Gly Lys Tyr Ala Asn Ile Pro Val Ile Ile Gly
                325                 330                 335

Asp Gln Asn Asp Glu Gly Thr Phe Phe Gly Thr Ser Ser Leu Asn Val
            340                 345                 350

Thr Thr Asp Ala Gln Ala Arg Glu Tyr Phe Lys Gln Ser Phe Val His
        355                 360                 365

Ala Ser Asp Ala Glu Ile Asp Thr Leu Met Thr Ala Tyr Pro Gly Asp
    370                 375                 380

Ile Thr Gln Gly Ser Pro Phe Asp Thr Gly Ile Leu Asn Ala Leu Thr
385                 390                 395                 400

Pro Gln Phe Lys Arg Ile Ser Ala Val Leu Gly Asp Leu Gly Phe Thr
                405                 410                 415

Leu Ala Arg Arg Tyr Phe Leu Asn His Tyr Thr Gly Gly Thr Lys Tyr
            420                 425                 430

Ser Phe Leu Ser Lys Gln Leu Ser Gly Leu Pro Val Leu Gly Thr Phe
        435                 440                 445

His Ser Asn Asp Ile Val Phe Gln Asp Tyr Leu Leu Gly Ser Gly Ser
    450                 455                 460

Leu Ile Tyr Asn Asn Ala Phe Ile Ala Phe Ala Thr Asp Leu Asp Pro
465                 470                 475                 480

Asn Thr Ala Gly Leu Leu Val Lys Trp Pro Glu Tyr Thr Ser Ser Ser
                485                 490                 495

Gln Ser Gly Asn Asn Leu Met Met Ile Asn Ala Leu Gly Leu Tyr Thr
            500                 505                 510

Gly Lys Asp Asn Phe Arg Thr Ala Gly Tyr Asp Ala Leu Phe Ser Asn
        515                 520                 525

Pro Pro Ser Phe Phe Val
    530
```

<210> SEQ ID NO 2
<211> LENGTH: 1602
<212> TYPE: DNA
<213> ORGANISM: Artificial Sequence
<220> FEATURE:
<223> OTHER INFORMATION: Codon optimized nucleotide sequence for
      expression in Pichia pastoris of the mature coding sequence of
      Lip1 of Candida rugosa

<400> SEQUENCE: 2

```
gccccaaccg ccactttggc taacggtgac accatcaccg gtttgaacgc catcatcaac      60
gaagccttct tgggtattcc atttgccgaa ccaccagttg gtaacttgag attcaaggac     120
ccagttccat actccggttc cttggatggt caaaagttca cttcttacgg tccatcttgt     180
atgcaacaaa acccagaagg tacctacgaa gaaaacttgc aaaggcagc tttagatctg     240 gttatgcaat ccaagttttt cgaagctgtt tctccatctt ctgaagactg tttgaccatt     300
aatgttgtta gaccacccgg gacaaaggct ggtgccaact tgccagttat gttgtggatc     360
```

```
tttggtggtg gttttgaagt tggtggtact agtaccttcc ctccagccca aatgattacc      420
aagtctattg ctatgggtaa gccaatcatc cacgtttctg tcaactacag agtctccagc      480
tggggtttct tggctggtga cgaaatcaag gccgaaggtt ctgccaacgc cggtttgaag      540
gaccaaagat tgggtatgca atgggtggct gacaacattg ctgcttttgg tggtgatcca      600
actaaggtta ctatctttgg tgaatctgct ggttctatgt ccgtcatgtg tcacattttg      660
tggaacgacg gtgacaacac ttacaagggt aagccattgt tcagagctgg tatcatgcaa      720
tctggtgcta tggttccatc tgacgccgtc gacggtatct acggtaacga aattttgac      780 ttgttggctt ccaacgctgg ttgtggttct gcctctgaca agttggcttg tttgagaggt      840
gtttcttctg cactttggaa gacgccacc aacaacaccc ctggtttctt ggcttactcc       900
tccttaagat tgtcttactt gccaagacca gacggtgtta acatcaccga cgacatgtac      960
gctttggtta gagaaggtaa gtatgccaac atccctgtta tcatcggtga ccaaaacgac     1020
gaaggtacct tctttggtac ttcttctttg aacgttacca ctgatgccca agccagagaa     1080
tatttcaagc aatcttttgt ccacgctagc gacgctgaaa tcgacacttt gatgactgct     1140
tacccaggtg acatcactca aggttctcca tttgacactg aattctaaa cgccttgacc      1200 ccacaattca agagaatctc tgctatcttg ggtgacttgg gttttacttt ggctcgtaga     1260
tacttcttga accactacac cggtggtacc aagtactctt tcttgtctaa gcaattgtct     1320
ggtttgccag ttttgggtac tttccactcc aacgatatcg tcttccaaga ctacttgttg     1380
ggttctggtt ccttgatcta caacaacgct ttcattgctt ttgccactga cttggaccca     1440
aacaccgccg gtttgttggt taagtggcca gaatacacct cttcttctca atctggtaac     1500
aacttgatga tgatcaacgc tttgggtttg tacaccggta aggacaactt cagaaccgcc     1560
ggttacgacg ctttgttctc caacccacca tctttctttg tt                         1602

<210> SEQ ID NO 3
<211> LENGTH: 2582
<212> TYPE: DNA
<213> ORGANISM: Komagataella phaffii
<220> FEATURE:
<221> NAME/KEY: source
<222> LOCATION: (1)..(2582)
<223> OTHER INFORMATION: strain ATCC 76273; HIS4 gene

<400> SEQUENCE: 3
aatacggctt cagaatttct caagactaca ctcactgtcc gacttcaagt atgacatttc        60
ccttgctacc tgcatacgca agtgttgcag agtttgataa ttccttgagt ttggtaggaa      120
aagccgtgtt tccctatgct gctgaccagc tgcacaacct gatcaagttc actcaatcga      180
ctgagcttca agttaatgtg caagttgagt catccgttac agaggaccaa tttgaggagc      240
tgatcgacaa cttgctcaag ttgtacaata atggtatcaa tgaagtgatt ttggacctag      300
atttggcaga aagagttgtc caaggatcc caggcgctag ggttatctat aggaccctgg      360
ttgataaagt tgcatccttg cccgctaatg ctagtatcgc tgtgccttt tcttctccac       420 tgggcgattt gaaaagtttc actaatggcg gtagtagaac tgtttatgct ttttctgaga      480
ccgcaaagtt ggtagatgtg acttccactg ttgcttctgg tataatcccc attattgatg      540
ctcggcaatt gactactgaa tacgaacttt ctgaagatgt caaaaagttc cctgtcagtg      600
aaattttgtt ggcgtctttg actactgacc gccccgatgg tctattcact actttggtgg      660
ctgactcttc taattactcg ttgggcctgg tgtactcgtc caaaaagtct attccggagg      720
```

```
ctataaggac acaaactgga gtctaccaat ctcgtcgtca cggttttgtgg tataaaggtg    780 ctacatctgg agcaactcaa aagttgctgg gtatcgaatt ggattgtgat ggagactgct    840
tgaaatttgt ggttgaacaa acaggtgttg gtttctgtca cttggaacgc acttcctgtt    900
ttggccaatc aaagggtctt agagccatgg aagccaccttt gtgggatcgt aagagcaatg   960
ctccagaagg ttcttatacc aaacggttat ttgacgacga agttttgttg aacgctaaaa   1020
ttagggagga agctgatgaa cttgcagaag ctaaatccaa ggaagatata gcctgggaat   1080
gtgctgactt attttatttt gcattagtta gatgtgccaa gtacggtgtg acgttggacg   1140
aggtggagag aaacctggat atgaagtccc taaaggtcac tagaaggaaa ggagatgcca   1200
agccaggata caccaaggaa caacctaaag aagaatccaa acctaaagaa gtcccttctg   1260
aaggtcgtat tgaattgtgc aaaattgacg tttctaaggc ctcctcacaa gaaattgaag   1320
atgcccttcg tcgtcctatc cagaaaacgg aacagattat ggaattagtc aaaccaattg   1380
tcgacaatgt tcgtcaaaat ggtgacaaag cccttttaga actaactgcc aagtttgatg   1440
gagtcgcttt gaagacacct gtgttagaag ctccttttccc agaggaactt atgcaattgc   1500
cagataacgt taagagagcc attgatctct ctatagataa cgtcaggaaa ttccatgaag   1560
ctcaactaac ggagacgttg caagttgaga cttgccctgg tgtagtctgc tctcgttttg   1620
caagacctat tgagaaagtt ggcctctata ttcctggtgg aaccgcaatt ctgccttcca   1680
cttccctgat gctgggtgtt cctgccaaag ttgctggtcg caaagaaatt gttttttgcat   1740 ctccacctaa gaaggatggt acccttaccc cagaagtcat ctacgttgcc cacaaggttg   1800
gtgctaagtg tatcgtgcta gcaggaggcg cccaggcagt agctgctatg gcttacggaa   1860
cagaaactgt tcctaagtgt gacaaaatat ttggtccagg aaaccagttc gttactgctg   1920
ccaagatgat ggttcaaaat gacacatcag ccctgtgtag tattgacatg cctgctgggc   1980
cttctgaagt tctagttatt gctgataaat acgctgatcc agatttcgtt gcctcagacc   2040
ttctgtctca agctgaacat ggtattgatt cccaggtgat tctgttggct gtcgatatga   2100
cagacaagga gcttgccaga attgaagatg ctgttcacaa ccaagctgtg cagttgccaa   2160
gggttgaaat tgtacgcaag tgtattgcac actctacaac cctatcggtt gcaacctacg   2220
agcaggcttt ggaaatgtcc aatcagtacg ctcctgaaca cttgatcctg caaatcgaga   2280
atgcttcttc ttatgttgat caagtacaac acgctggatc tgtgtttgtt ggtgcctact   2340
ctccagagag ttgtggagat tactcctccg gtaccaacca cactttgcca acgtacggat   2400
atgcccgtca atacagcgga gttaacactg caaccttcca gaagttcatc acttcacaag   2460
acgtaactcc tgagggactg aaacatattg gccaagcagt gatggatctg ctgctgttg    2520 aaggtctaga tgctcaccgc aatgctgtta aggttcgtat ggagaaactg ggacttattt   2580
aa                                                                  2582
```

<210> SEQ ID NO 4
<211> LENGTH: 34
<212> TYPE: DNA
<213> ORGANISM: Artificial Sequence
<220> FEATURE:
<223> OTHER INFORMATION: Nucleotide sequence of an 34 bp FRT
      recombination site

<400> SEQUENCE: 4

```
gaagttccta tactttctag agaataggaa cttc                                34
```

<210> SEQ ID NO 5

```
<211> LENGTH: 4
<212> TYPE: PRT
<213> ORGANISM: Artificial Sequence
<220> FEATURE:
<223> OTHER INFORMATION: Glutamine Alanine repeat

<400> SEQUENCE: 5

Glu Ala Glu Ala
1

<210> SEQ ID NO 6
<211> LENGTH: 89
<212> TYPE: PRT
<213> ORGANISM: Artificial Sequence
<220> FEATURE:
<223> OTHER INFORMATION: alpha-mating factor from S. cerevisiae followed
      by a Kex2 processing site (KR) and Glutamine Alanine repeat

<400> SEQUENCE: 6

Met Arg Phe Pro Ser Ile Phe Thr Ala Val Leu Phe Ala Ala Ser Ser
1               5                   10                  15

Ala Leu Ala Ala Pro Val Asn Thr Thr Thr Glu Asp Glu Thr Ala Gln
            20                  25                  30

Ile Pro Ala Glu Ala Val Ile Gly Tyr Ser Asp Leu Glu Gly Asp Phe
        35                  40                  45

Asp Val Ala Val Leu Pro Phe Ser Asn Ser Thr Asn Asn Gly Leu Leu
    50                  55                  60

Phe Ile Asn Thr Thr Ile Ala Ser Ile Ala Lys Glu Glu Gly Val
65                  70                  75                  80

Ser Leu Glu Lys Arg Glu Ala Glu Ala
                85

<210> SEQ ID NO 7
<211> LENGTH: 1650
<212> TYPE: DNA
<213> ORGANISM: Artificial Sequence
<220> FEATURE:
<223> OTHER INFORMATION: Nucleotide sequence encoding Kex2 processing
      site, followed by Glu Ala repeat and codon optimized C. rugosa 534
      w.t. lipase (LIP1) with additional XhoI and NotI sites at 5' and
      3' ends, respectively

<400> SEQUENCE: 7
ctcgagaaga gagaggccga agctgcccca accgccactt tggctaacgg tgacaccatc      60
accggtttga acgccatcat caacgaagcc ttcttgggta ttccatttgc cgaaccacca     120
gttggtaact tgagattcaa ggacccagtt ccatactccg ttccttgga tggtcaaaag      180 ttcacttctt acgtccatc ttgtatgcaa caaaacccag aaggtaccta cgaagaaaac     240
ttgccaaagg cagctttaga tctggttatg caatccaaag ttttcgaagc tgtttctcca     300
tcttctgaag actgtttgac cattaatgtt gttagaccac ccgggacaaa ggctggtgcc     360
aacttgccag ttatgttgtg gatcttggt ggtggttttg aagttggtgg tactagtacc     420
ttccctccag cccaaatgat taccaagtct attgctatgg gtaagccaat catccacgtt     480
tctgtcaact acagagtctc cagctgggggt ttcttggctg gtgacgaaat caaggccgaa     540
ggttctgcca acgccggttt gaaggaccaa agattgggta tgcaatgggt ggctgacaac     600
attgctgctt tggtggtgga tccaactaag ttactatct tggtgaatc tgctggttct     660 atgtccgtca tgtgtcacat tttgtggaac gacggtgaca cacttacaa gggtaagcca     720 ttgttcagag ctggtatcat gcaatctggt gctatggtc catctgacgc cgtcgacggt     780
```

```
atctacggta acgaaatttt tgacttgttg gcttccaacg ctggttgtgg ttctgcctct    840
gacaagttgg cttgtttgag aggtgtttct tctgacactt tggaagacgc caccaacaac    900 accccctggtt tcttggctta ctcctcctta agattgtctt acttgccaag accagacggt   960
gttaacatca ccgacgacat gtacgctttg gttagagaag gtaagtatgc caacatccct    1020
gttatcatcg gtgaccaaaa cgacgaaggt accttctttg gtacttcttc tttgaacgtt    1080
accactgatg cccaagccag agaatatttc aagcaatctt ttgtccacgc tagcgacgct    1140
gaaatcgaca ctttgatgac tgcttaccca ggtgacatca ctcaaggttc tccatttgac    1200
actggaattc taaacgcctt gaccccacaa ttcaagagaa tctctgctat cttgggtgac    1260
ttgggtttta ctttggctcg tagatacttc ttgaaccact acaccggtgg taccaagtac    1320
tctttcttgt ctaagcaatt gtctggtttg ccagtttgg gtactttcca ctccaacgat     1380
atcgtcttcc aagactactt gttgggttct ggttccttga tctacaacaa cgctttcatt    1440
gcttttgcca ctgacttgga cccaaacacc gccggtttgt tggttaagtg gccagaatac    1500
acctcttctt ctcaatctgg taacaacttg atgatgatca acgctttggg tttgtacacc    1560
ggtaaggaca acttcagaac cgccggttac gacgctttgt tctccaaccc accatctttc    1620
tttgtttaat aaggttaaag gggcggccgc                                     1650
```

MUTANT LIPASE AND USE THEREOF

CROSS-REFERENCE TO RELATED APPLICATIONS

This application is a National Stage entry of International Application No. PCT/EP2017/063919, filed 8 Jun. 2017, which claims priority to European Patent Application No. 16173955.2, filed 10 Jun. 2016.

REFERENCE TO SEQUENCE LISTING SUBMITTED AS A COMPLIANT ASCII TEXT FILE (.TXT)

Pursuant to the EFS-Web legal framework and 37 CFR §§ 1.821-825 (see MPEP § 2442.03(a)), a Sequence Listing in the form of an ASCII-compliant text file (entitled "2919208-491000_Sequence_Listing_ST25.txt" created on 28 Nov. 2018, and 14,688 bytes in size) is submitted concurrently with the instant application, and the entire contents of the Sequence Listing are incorporated herein by reference.

BACKGROUND

The present invention relates to a polypeptide having lipase activity, a composition comprising the polypeptide as disclosed herein, a nucleic acid encoding a polypeptide having a lipase activity, an expression vector, a recombinant host cell, a method for preparing a recombinant polypeptide having lipase activity and a process for preparing a product wherein the lipase is used.

DESCRIPTION OF RELATED ART

Lipases (triacylglycerol acyl hydrolase, EC 3.1.1.3) and esterase (EC 3.1.1.1.) are part of the hydrolase families that catalyze the hydrolysis of lipids such as fat and oil.

Traditionally the dairy industry uses animal derived lipases for flavor enhancement of dairy products. These animal lipases have a preference for short-chain fatty acids (C4, C6), which is advantageous for avoiding a soapy flavor caused by long-chain fatty acids such as palmitic acid and/or octadecanoic acid.

Nowadays there is an increasing demand for replacing animal derived lipases with microbial derived lipases. Microbial lipases can for instance be derived from the yeast *Candida rugosa*.

*Candida rugosa* lipases are widely used in industry and several lipase amino acid sequences have been identified (Akoh, et al. (2004), Lipids, Vol. 39, No. 6, p. 513-526). However, *Candida rugosa* lipases typically have a preference for long chain fatty acids.

WO2015087833 discloses a mutant lipase from *Candida rugosa* which has a preference for short to medium chain fatty acids. The mutant lipase has a mutation at position 428 and/or position 429.

Schmitt, J. et al, Protein Engineering, Vol 15, No. 7, pp. 595-601 (2002) discloses *Candida rugosa* lipase mutants with different chain length specificities. The Lip1 lipase mutant P246F showed significantly higher activity on tributyrin (C4) and tricaproin (C6) as compared to the wild type lipase, resulting in higher ratio's C4/C8 and C6/C8 than the wild type lipase.

There is a need for further mutant *Candida rugosa* lipases which show a higher preference for short chain fatty acids (C4, C6) compared to medium and long chain fatty acids (C8 and higher).

SUMMARY

The present invention relates to a polypeptide having lipase activity wherein the polypeptide is
 a. a polypeptide, which, when aligned with the polypeptide according to SEQ ID NO: 1 comprises at least one amino acid substitution resulting in Ser (S), Ala (A) or Leu (L) at position 246, Trp (W) at position 307, Leu (L) at position 345, Ile (I) at position 365, and/
 b. or Phe (F) at position 534, wherein the position is defined with reference to SEQ ID NO: 1, wherein Ala(A) at position 1 in SEQ ID NO: 1 is counted as number 1; or,
 c. a polypeptide comprising an amino acid sequence according to SEQ ID NO: 1, wherein SEQ ID NO: 1 comprises at least one amino acid substitution P246A, P246L, P246S, L307W, F345L, S365I, and/or V534F, wherein the substitutions are defined with reference to SEQ ID NO: 1, wherein Ala (A) at position 1 in SEQ ID NO: 1 is counted as number 1; or,
 d. a polypeptide according to a) or b), wherein the polypeptide has at least 80%, 85%, 90%, 91%, 92%, 93%, 94%, 95%, 96%, 97%, 98%% or 99% identity to the amino acid sequence of SEQ ID NO: 1; or,
 e. a polypeptide encoded by a nucleic acid which has at least 80%, 85%, 90%, 91%, 92%, 93%, 94%, 95%, 96%, 97%, 98%, or 99% identity to the nucleotide sequence of SEQ ID NO: 2, wherein SEQ ID NO: 2 comprises at least one mutation resulting in an amino acid Ser (S), Ala (A) or Leu (L) at position 246, Trp (W) at position 307, Leu (L) at position 345, Ile (I) at position 365, and/or Phe (F) at position 534 of a polypeptide according to SEQ ID NO: 1, wherein Ala (A) at position 1 in SEQ ID NO: 1 is counted as number 1; or,
 f. a polypeptide encoded by a nucleic acid comprising a sequence that hybridizes under low, medium and/or high stringency conditions to the complementary strand of the nucleic acid sequence of SEQ ID NO: 2.

In another aspect the present disclosure relates to a composition comprising a polypeptide as disclosed herein.

In another aspect a method for generating a variant polypeptide is disclosed wherein the method comprises
 a. selecting a parent polypeptide comprising at least 80%, 85%, 90%, 91%, 92%, 93%, 94%, 95%, 96%, 97%, 98%, 99% or 100% identity to the amino acid sequence according to SEQ ID NO: 1; and,
 b. substituting at least one amino acid into Ser (S), Ala (A) or Leu (L) at position 246, Trp (W) at position 307, Leu (L) at position 345, Ile (I) at position 365, and/or Phe (F) at position 534, wherein said position is defined with reference to SEQ ID NO: 1, wherein Ala(A) at position 1 in SEQ ID NO: 1 is counted as number 1; and
 c. generating the variant polypeptide, wherein the polypeptide having lipase activity has a higher specificity towards butyrate than the specificity towards octanoate and/or palmitate.

The present disclosure also relates to a mutant nucleic acid encoding a lipase, an expression vector comprising a nucleic acid as disclosed herein and a recombinant host cell comprising a nucleic acid disclosed herein, or an expression vector according disclosed herein.

In another aspect the present disclosure relates to a method for preparing a polypeptide having lipase activity as disclosed herein, comprising cultivating a host cell in a suitable fermentation medium, under conditions that allow expression of the polypeptide, and preparing the polypeptide, and optionally recovering the polypeptide.

In another aspect the present disclosure relates to a process for preparing a product comprising a lipid, comprising bringing an intermediate form of a product into contact with a polypeptide having lipase activity as disclosed herein, or a composition comprising a polypeptide having lipase activity, and preparing the product.

BRIEF DESCRIPTION OF THE DRAWINGS

FIG. 1 is a physical map of the integration expression vector, pD902-LIP1.

DETAILED DESCRIPTION OF A PREFERRED EMBODIMENT

Definitions

Amino acids are indicated by their full name, three letter code or one letter abbreviations which are known to a person skilled in the art.

The term "complementary strand" can be used interchangeably with the term "complement". The complement of a nucleic acid strand can be the complement of a coding strand or the complement of a non-coding strand. When referring to double-stranded nucleic acids, the complement of a nucleic acid encoding a polypeptide refers to the complementary strand of the strand encoding the amino acid sequence or to any nucleic acid molecule containing the same.

The term "control sequence" can be used interchangeably with the term "expression-regulating nucleic acid sequence". The term as used herein refers to nucleic acid sequences necessary for and/or affecting the expression of an operably linked coding sequence in a particular host organism or in vitro. When two nucleic acid sequences are operably linked, they usually will be in the same orientation, and also in the same reading frame. They usually will be essentially contiguous, although this may not be required. The expression-regulating nucleic acid sequences, such as inter alia appropriate transcription initiation, termination, promoter, leader, signal peptide, propeptide, prepropeptide, or enhancer sequences; Shine-Dalgarno sequence, repressor or activator sequences; efficient RNA processing signals such as splicing and polyadenylation signals; sequences that stabilize cytoplasmic mRNA; sequences that enhance translation efficiency (e.g., ribosome binding sites); sequences that enhance protein stability; and when desired, sequences that enhance protein secretion, can be any nucleic acid sequence showing activity in the host organism of choice and can be derived from genes encoding proteins, which are either endogenous or heterologous to a host cell. Each control sequence may be native or foreign to the nucleic acid sequence encoding the polypeptide. When desired, the control sequence may be provided with linkers for the purpose of introducing specific restriction sites facilitating ligation of the control sequences with the coding region of the nucleic acid sequence encoding a polypeptide. Control sequences may be optimized to their specific purpose.

A "dairy product" refers to any kind of milk-based product intended to be used as food, feed or beverage, including but not limited to, cheese, milk, skimmed milk, acidified milk, butter milk, condensed milk, spreads, margarines, yoghurt, ice cream, milk powder, butter, EMC (Enzyme Modified Cheese), dulce de leche, coffee whitener; coffee creamer, cream, ghee, dairy analogue, etcetera.

Cheese may be any kind of cheese, e.g. fresh cheese, hard cheese, curd cheese, cream cheese, white mould cheese, blue mould cheese and processed cheese. Examples of fresh cheese are Ricotta, Cream cheese, Neufchatel or Cottage cheese. Examples of hard cheese are Chester, Danbo, Manchego, Saint Paulin, Cheddar, Monterey, Colby, Edam, Gouda, Muenster, Swiss type, Gruyere, Emmenthaler, Parmigiano Reggiano, Grana Padano, Parmesan, Pecorino, Provolone, and Romano. Examples of curd cheese such as Feta cheese, Quotija cheese, pasta filata cheese such as Mozzarella, and Queso fresco cheese. Examples of cream cheese are Philadelphia cheese. Examples of white mould cheese are Brie and Camembert cheese. Examples of blue mould cheese are Gorgonzola and Danish blue cheese.

As used herein, the term "endogenous" refers to a nucleic acid or amino acid sequence naturally occurring in a host.

The term "expression" includes any step involved in the production of the polypeptide including, but not limited to, transcription, post transcriptional modification, translation, post-translational modification, and secretion.

Polynucleotides of the present invention as described herein may be over-expressed in a host cell of the invention compared to a parent cell in which said gene is not over-expressed. Over-expression of a polynucleotide sequence is defined herein as the expression of the said sequence gene which results in an activity of the polypeptide encoded by the said sequence in a host cell being at least 1.1, at least 1.25 or at least 1.5-fold the activity of the polypeptide in the host cell; preferably the activity of said polypeptide is at least 2-fold, more preferably at least 3-fold, more preferably at least 4-fold, more preferably at least 5-fold, even more preferably at least 10-fold and most preferably at least 20-fold the activity of the polypeptide in the parent cell.

An "expression vector" comprises a polynucleotide coding for a polypeptide, such as a polypeptide according to the present invention, operably linked to the appropriate control sequences (such as a promoter, and transcriptional and translational stop signals) for expression and/or translation in vitro, or in a host cell of the polynucleotide.

The expression vector may be any vector (e.g., a plasmid or virus), which can be conveniently subjected to recombinant DNA procedures and can bring about the expression of the polynucleotide. The choice of the vector will typically depend on the compatibility of the vector with the cell into which the vector is to be introduced. The vectors may be linear or closed circular plasmids. The vector may be an autonomously replicating vector, i.e., a vector, which exists as an extra-chromosomal entity, the replication of which is independent of chromosomal replication, e.g., a plasmid, an extra-chromosomal element, a mini-chromosome, or an artificial chromosome. Alternatively, the vector may be one which, when introduced into the host cell, is integrated into the genome and replicated together with the chromosome(s) into which it has been integrated. The integrative cloning vector may integrate at random or at a predetermined target locus in the chromosomes of the host cell. The vector system may be a single vector or plasmid or two or more vectors or plasmids, which together contain the total DNA to be introduced into the genome of the host cell, or a transposon. A vector of the invention may comprise one, two or more, for example three, four or five polynucleotides of the invention, for example for overexpression.

A host cell as defined herein is an organism suitable for genetic manipulation and one which may be cultured at cell densities useful for industrial production of a target product, such as a polypeptide according to the present invention. A host cell may be a host cell found in nature or a host cell derived from a parent host cell after genetic manipulation or classical mutagenesis. Advantageously, a host cell is a recombinant host cell. A host cell may be a prokaryotic, archaebacterial or eukaryotic host cell. A prokaryotic host cell may be, but is not limited to, a bacterial host cell. A eukaryotic host cell may be, but is not limited to, a yeast, a fungus, an amoeba, an algae, a plant, an animal, or an insect host cell.

The term "heterologous" as used herein refers to nucleic acid or amino acid sequences not naturally occurring in a host cell. In other words, the nucleic acid or amino acid sequence is not identical to that naturally found in the host cell.

The term "hybridization" means the pairing of substantially complementary strands of oligomeric compounds, such as nucleic acid compounds. Hybridization may be performed under low, medium or high stringency conditions. Low stringency hybridization conditions comprise hybridizing in 6× sodium chloride/sodium citrate (SSC) at about 45° C., followed by two washes in 0.2×SSC, 0.1% SDS at least at 50° C. (the temperature of the washes can be increased to 55° C. for low stringency conditions). Medium stringency hybridization conditions comprise hybridizing in 6×SSC at about 45° C., followed by one or more washes in 0.2×SSC, 0.1% SDS at 60° C., and high stringency hybridization conditions comprise hybridizing in 6×SSC at about 45° C., followed by one or more washes in 0.2×SSC, 0.1% SDS at 65° C.

An "isolated nucleic acid fragment" is a nucleic acid fragment that is not naturally occurring as a fragment and would not be found in the natural state.

The term "isolated polypeptide" as used herein means a polypeptide that is removed from at least one component, e.g. other polypeptide material, with which it is naturally associated. The isolated polypeptide may be free of any other impurities. The isolated polypeptide may be at least 50% pure, e.g., at least 60% pure, at least 70% pure, at least 75% pure, at least 80% pure, at least 85% pure, at least 90% pure, or at least 95% pure, 96%, 97%, 98%, 99%, 99.5%, 99.9% as determined by SDS-PAGE or any other analytical method suitable for this purpose and known to the person skilled in the art. An isolated polypeptide may be produced by a recombinant host cell.

A "lipase", also referred to as a lipolytic enzyme, is an enzyme that catalyzes the hydrolysis of fats (lipids). An enzyme having lipase activity as used herein comprises hydrolytic activity towards triacylglycerol, such a lipase activity with enzyme classification EC 3.1.1.3, and may also be referred to as an enzyme having esterase activity, such as an esterase with enzyme classification EC 3.1.1.1. An enzyme having lipase activity as used herein may also comprises hydrolytic activity towards a galactolipid, such as a galactolipase activity with enzyme classification EC. 3.1.1.26, and/or towards phospholipids, such as a phospholipase activity with enzyme classification (EC 3.1.1.4, EC 3.1.1.5, EC 3.1.1.32). Typically an enzyme having lipase activity, as used herein comprises hydrolytic activity towards triacylglycerol. The specificity of the lipase can be shown through in vitro assay making use of appropriate substrate, for example triacylglycerol lipid, phosphatidylcholine and digalactosyldiglyceride.

A lipid, herein synonymous to "lipids", refer to fats or oil, including galactolipids and phospholipids. Lipids also comprise triglycerides, diglycerides and monoglycerides. The word "triglycerides" is synonymous to "triacylglycerol". In these compounds the hydroxyl groups of glycerol are esterified with fatty acids.

A nucleic acid or polynucleotide sequence is defined herein as a nucleotide polymer comprising at least 5 nucleotide or nucleic acid units. A nucleotide or nucleic acid refers to RNA and DNA. The terms "nucleic acid" and "polynucleotide sequence" are used interchangeably herein.

A "peptide" refers to a short chain of amino acid residues linked by a peptide (amide) bonds. The shortest peptide, a dipeptide, consists of 2 amino acids joined by single peptide bond.

The term "polypeptide" refers to a molecule comprising amino acid residues linked by peptide bonds and containing more than five amino acid residues. The term "protein" as used herein is synonymous with the term "polypeptide" and may also refer to two or more polypeptides. Thus, the terms "protein" and "polypeptide" can be used interchangeably. Polypeptides may optionally be modified (e.g., glycosylated, phosphorylated, acylated, farnesylated, prenylated, sulfonated, and the like) to add functionality. Polypeptides exhibiting activity in the presence of a specific substrate under certain conditions may be referred to as enzymes. It will be understood that, as a result of the degeneracy of the genetic code, a multitude of nucleotide sequences encoding a given polypeptide may be produced.

A "mature polypeptide" is defined herein as a polypeptide in its final form and is obtained after translation of a mRNA into polypeptide and post-translational modifications of said polypeptide. Post-translational modification includes N-terminal processing, C-terminal truncation, glycosylation, phosphorylation and removal of leader sequences such as signal peptides, propeptides and/or prepropeptides by cleavage.

A "mature polypeptide coding sequence" means a polynucleotide that encodes a mature polypeptide.

The term "nucleic acid construct" is herein referred to as a nucleic acid molecule, either single- or double-stranded, which is isolated from a naturally occurring gene or which has been modified to contain segments of nucleic acid which are combined and juxtaposed in a manner which would not otherwise exist in nature. The term nucleic acid construct is synonymous with the term "expression cassette" or "expression vector" when the nucleic acid construct contains all the control sequences required for expression of a coding sequence, wherein said control sequences are operably linked to said coding sequence.

The term "promoter" is defined herein as a DNA sequence that binds RNA polymerase and directs the polymerase to the correct downstream transcriptional start site of a nucleic acid sequence to initiate transcription.

The term "recombinant" when used in reference to a cell, nucleic acid, protein or vector, indicates that the cell, nucleic acid, protein or vector, has been modified by the introduction of a heterologous nucleic acid or protein or the alteration of a native nucleic acid or protein, or that the cell is derived from a cell so modified. Thus, for example, recombinant cells express genes that are not found within the native (non-recombinant) form of the cell or express native genes that are otherwise abnormally expressed, underexpressed or not expressed at all. The term "recombinant" is synonymous with "genetically modified" and "transgenic".

"Sequence identity", or sequence homology are used interchangeable herein. For the purpose of this invention, it is defined here that in order to determine the percentage of sequence homology or sequence identity of two amino acid sequences or of two nucleic acid sequences, the sequences are aligned for optimal comparison purposes. In order to optimize the alignment between the two sequences gaps may be introduced in any of the two sequences that are compared.

Such alignment can be carried out over the full length of the sequences being compared. Alternatively, the alignment may be carried out over a shorter length, for example over about 20, about 50, about 100 or more nucleic acids/bases or amino acids. The sequence identity is the percentage of identical matches between the two sequences over the reported aligned region. The percent sequence identity between two amino acid sequences or between two nucleotide sequences may be determined using the Needleman and Wunsch algorithm for the alignment of two sequences. (Needleman, S. B. and Wunsch, C. D. (1970) J. Mol. Biol. 48, 443-453). Both amino acid sequences and nucleotide sequences can be aligned by the algorithm. The Needleman-Wunsch algorithm has been implemented in the computer program NEEDLE. For the purpose of this invention the NEEDLE program from the EMBOSS package was used (version 2.8.0 or higher, EMBOSS: The European Molecular Biology Open Software Suite (2000) Rice, P. Longden, I. and Bleasby, A. Trends in Genetics 16, (6) pp 276-277, http://emboss.bioinformatics.nl/). For protein sequences EBLOSUM62 is used for the substitution matrix. For nucleotide sequence, EDNAFULL is used. The optional parameters used are a gap-open penalty of 10 and a gap extension penalty of 0.5. The skilled person will appreciate that all these different parameters will yield slightly different results but that the overall percentage identity of two sequences is not significantly altered when using different algorithms.

After alignment by the program NEEDLE as described above the percentage of sequence identity between a query sequence and a sequence of the invention is calculated as follows: Number of corresponding positions in the alignment showing an identical amino acid or identical nucleotide in both sequences divided by the total length of the alignment after subtraction of the total number of gaps in the alignment. The identity as defined herein can be obtained from NEEDLE by using the NOBRIEF option and is labeled in the output of the program as "longest-identity".

The nucleic acid and protein sequences of the present invention can further be used as a "query sequence" to perform a search against public databases to, for example, identify other family members or related sequences. Such searches can be performed using the NBLAST and XBLAST programs (version 2.0) of Altschul, et al. (1990) J. Mol. Biol. 215:403-10. BLAST nucleotide searches can be performed with the NBLAST program, score=100, word length=12 to obtain nucleotide sequences homologous to nucleic acid molecules of the invention. BLAST protein searches can be performed with the XBLAST program, score=50, wordlength=3 to obtain amino acid sequences homologous to protein molecules of the invention. To obtain gapped alignments for comparison purposes, Gapped BLAST can be utilized as described in Altschul et al., (1997) Nucleic Acids Res. 25(17): 3389-3402. When utilizing BLAST and Gapped BLAST programs, the default parameters of the respective programs (e.g., XBLAST and NBLAST) can be used. See the homepage of the National Center for Biotechnology Information at http://www.ncbi.nlm.nih.gov/.

The term "substantially pure" with regard to polypeptides refers to a polypeptide preparation which contains at the most 50% by weight of other polypeptide material. The polypeptides disclosed herein are preferably in a substantially pure form. In particular, it is preferred that the polypeptides disclosed herein are in "essentially pure form", i.e. that the polypeptide preparation is essentially free of other polypeptide material. Optionally, the polypeptide may also be essentially free of non-polypeptide material such as nucleic acids, lipids, media components, and the like. Herein, the term "substantially pure polypeptide" is synonymous with the terms "isolated polypeptide" and "polypeptide in isolated form". The term "substantially pure" with regard to polynucleotide refers to a polynucleotide preparation which contains at the most 50% by weight of other polynucleotide material. The polynucleotides disclosed herein are preferably in a substantially pure form. In particular, it is preferred that the polynucleotide disclosed herein are in "essentially pure form", i.e. that the polynucleotide preparation is essentially free of other polynucleotide material. Optionally, the polynucleotide may also be essentially free of non-polynucleotide material such as polypeptides, lipids, media components, and the like. Herein, the term "substantially pure polynucleotide" is synonymous with the terms "isolated polynucleotide" and "polynucleotide in isolated form".

A "substitution" as used herein in relation to polypeptides or nucleic acids, denotes the replacement of one or more amino acids in a polypeptide sequence or of one or more nucleotides in a polynucleotide sequence, respectively, by different amino acids or nucleotides, respectively. For instance, a substitution indicates that a position in a polypeptide as disclosed herein, such as a variant polypeptide, which corresponds to at least one position set out above in SEQ ID NO: 1, comprises an amino acid residue which does not appear at that position in the parent polypeptide (for instance the parent sequence SEQ ID NO: 1).

A "synthetic molecule", such as a synthetic nucleic acid or a synthetic polypeptide is produced by in vitro chemical or enzymatic synthesis. It includes, but is not limited to, variant nucleic acids made with optimal codon usage for host organisms of choice.

A synthetic nucleic acid may be optimized for codon use, preferably according to the methods described in WO2006/077258 and/or WO2008000632, which are herein incorporated by reference. WO2008/000632 addresses codon-pair optimization. Codon-pair optimization is a method wherein the nucleotide sequences encoding a polypeptide that have been modified with respect to their codon-usage, in particular the codon-pairs that are used, are optimized to obtain improved expression of the nucleotide sequence encoding the polypeptide and/or improved production of the encoded polypeptide. Codon pairs are defined as a set of two subsequent triplets (codons) in a coding sequence. Those skilled in the art will know that the codon usage needs to be adapted depending on the host species, possibly resulting in variants with significant homology deviation from SEQ ID NO: 2, but still encoding the polypeptide according to the invention.

As used herein, the terms "variant", "derivative", "mutant" or "homologue" can be used interchangeably. They can refer to either polypeptides or nucleic acids. Variants include substitutions, insertions, deletions, truncations, transversions, and/or inversions, at one or more locations relative to a reference sequence. Variants can be made for example by site-saturation mutagenesis, scanning mutagenesis, insertional mutagenesis, random mutagenesis, site-directed mutagenesis, and directed-evolution, as well as various other recombination approaches known to a skilled person in the art. Variant genes of nucleic acids may be synthesized artificially by known techniques in the art.

FIGURES

FIG. 1. Physical map of the integration expression vector, pD902-LIP1. The XhoI and NotI sites were used to introduce the lip1 lipase gene. The digestion with SacI targets the integration to the AOX1 site in *Pichia pastoris*. Transformants were selected on zeocin.

SEQUENCES

SEQ ID NO: 1: Mature amino acid sequence of Lip1 of *Candida rugosa*.
SEQ ID NO: 2: A codon optimized mature encoding nucleotide sequence of Lip1 of *Candida rugosa* for expression in *Pichia pastoris*.
SEQ ID NO: 3: HIS4 gene from *Komagataella phaffii* strain ATCC 76273.
SEQ ID NO: 4: Nucleotide sequence of the 34 bp FRT recombination site
SEQ ID NO: 5: Glutamine Alanine repeat
SEQ ID NO: 6: α-mating factor from *Saccharomyces cerevisiae* followed by a Kex2 processing site (KR) and Glutamine Alanine repeat (SEQ ID NO:5)
SEQ ID NO: 7: Nucleotide sequence encoding a Kex2 processing site followed by the Glutamine Alanine repeat and the codon optimized *Candida rugosa* 534 wild type lipase (LIP1) with an additional XhoI site and NotI site at the 5' and 3' ends, respectively.

The present disclosure relates to a polypeptide having lipase activity with an altered substrate specificity.

In one aspect the present disclosure relates to a polypeptide having lipase activity wherein the polypeptide is
  a. a polypeptide, which, when aligned with the polypeptide according to SEQ ID NO: 1, comprises at least one amino acid substitution resulting in Ser (S), Ala (A) or Leu (L) at position 246, Trp (W) at position 307, Leu (L) at position 345, Ile (I) at position 365, and/or Phe (F) at position 534, wherein Ala (A) at position 1 in SEQ ID NO: 1 is counted as number 1; or,
  b. a polypeptide comprising an amino acid sequence according to SEQ ID NO:1, wherein SEQ ID NO: 1 comprises at least one amino acid substitution P246A, P246L, P246S, L307W, F345L, S365I, and/or V534F; or,
  c. a polypeptide according to a) or b), wherein the polypeptide has at least 80%, 85%, 90%, 91%, 92%, 93%, 94%, 95%, 96%, 97%, 98%% or 99% identity to amino acid sequence of SEQ ID NO: 1; or,
  d. a polypeptide encoded by a nucleic acid which has at least 80%, 85%, 90%, 91%, 92%, 93%, 94%, 95%, 96%, 97%, 98%, or 99% to the nucleotide sequence of SEQ ID NO: 2, wherein SEQ ID NO: 2 comprises at least one mutation resulting in an amino acid Ser (S), Ala (A) or Leu (L) at position 246, Trp (W) at position 307, Leu (L) at position 345, Ile (I) at position 365, and/or Phe (F) at position 534 of a polypeptide according to SEQ ID NO: 1, wherein Ala (A) at position 1 in SEQ ID NO: 1 is counted as number 1; or,
  e. a polypeptide encoded by a nucleic acid comprising a sequence that hybridizes under low, medium and/or high stringency conditions to the complementary strand of the mature polypeptide encoding sequence of SEQ ID NO: 2.

Surprisingly a polypeptide having a lipase activity as disclosed herein has a higher specificity towards short chain fatty acids, such as butyrate (C4) than the specificity towards longer chain fatty acids, such as octanoate (C8) and palmitate (C16). This is advantageous to avoid or reduce generation of a soapy flavour in a food product, such as in dairy products.

The combination of a) and b) as described above plus the surprising effect, results in a polypeptide having lipase activity wherein the polypeptide is a variant polypeptide of SEQ ID NO: 1 and at least comprises one amino acid substitution resulting in Ser (S), Ala (A) or Leu (L) at position 246, Trp (W) at position 307, Leu (L) at position 345, Ile (I) at position 365 or Phe (F) at position 534, wherein Ala (A) at position 1 in SEQ ID NO: 1 is counted as number 1, wherein said variant has at least 80%, 85%, 90%, 91%, 92%, 93%, 94%, 95%, 96%, 97%, 98%% or 99% identity to amino acid sequence of SEQ ID NO: 1 and wherein said variant has a higher specific towards butyrate as a side chain than the specificity towards octanoate and/or palmitate as a side chain.

Lipase activity as used herein relates to an enzymatic activity that hydrolyses a lipid such as a triacylglycerol, a phospholipid or a galactolipid.

Lipase specificity as used herein relates to a polypeptide having lipase activity where the activity is specified towards a fatty acid side chain of a lipid, for instance lipids with butyrate, octanoate or palmitate as a side chain. For instance, a lipase specificity towards butyrate relates to a lipase having activity towards a lipid wherein at least one of the hydroxyl groups of glycerol is esterified with butyrate.

A higher specificity towards butyrate than towards octanoate as used herein means that the specificity of a polypeptide having a lipase activity towards butyrate as a side chain is at least two, three, four, five, ten, fifteen, twenty, or twenty-five or at least thirty times higher than the specificity towards octanoate as a side chain.

A higher specificity towards butyrate than towards palmitate as used herein means that the specificity of the polypeptide having lipase activity towards butyrate as a side chain is at least two, three, four, five, ten, fifteen, twenty, twenty-five or at least thirty times higher than the specificity towards palmitate as a side chain.

Comparing the specificity of a polypeptide having lipase activity on a lipid having butyrate, octanoate or palmitate as a side chain may be performed by measuring the lipase activity towards tributyrate (tributyrin), tripalmitate (tripalmitin), trioctanoate (trioctanoin) as a substrate at pH 5.0 at a temperature of 37 degrees Celsius as disclosed in the Examples, and comparing the activities.

Alternatively, comparing the specificity of a polypeptide having lipase activity on a lipid comprising butyrate, octanoate or palmitate as a side chain may be performed by measuring the lipase activity towards paranitrophenyl (pNP) butyrate and paranitrophenyl (pNP) octanoate or paranitrophenyl (pNP) palmitate at a pH of 4.5 and a temperature of 25 degrees Celsius as disclosed in the Examples, and comparing the activities.

Instead of using a synthetic substrate to test the specificity one can also use a non-synthetic substrate such as an oil or fat comprising substrate. Alternatively, comparing the specificity of a polypeptide having lipase activity may be performed on a non-synthetic (i.e. natural) substrate (for example an oil or fat comprising substrate)—including C4- and compare the fatty acid release of a polypeptide according to the invention with a wild-type, i.e. non-mutated, enzyme. An example of a non-synthetic substrate is an oil or fat comprising substrate such as—but not limited to—milk, milk cream, butter fat or processed cheese.

Independent of the substrate used, the most important selection criteria for selecting a polypeptide according to the invention is the ratio C4/C16. The ratio C4/C8 is less relevant. Preferably, a variant according to the invention has a higher specific towards butyrate as a side chain than the specificity towards palmitate as a side chain Advantageously, the ratio of the specificity of a polypeptide having lipase activity comprising an amino acid substitution as disclosed herein towards butyrate as a side chain compared to the specificity towards octanoate and/or palmitate as a side chain is higher than this ratio of butyrate versus octanoate or palmitate of a corresponding wild type polypeptide having a lipase activity. Preferably, this ratio of the specificity of a polypeptide having lipase activity comprising an amino acid substitution as disclosed herein towards butyrate as a side chain compared to the specificity of towards octanoate or palmitate as a side chain is at least 2, 3, 4, 5, 10, 15, 20, or 30 times higher than this ratio of a corresponding wild type polypeptide having lipase activity. A preferred wild type polypeptide having lipase activity is SEQ ID NO:1.

A polypeptide having lipase activity is also referred to as a lipase, or a lipolytic enzyme.

A polypeptide having lipase activity may be a polypeptide, which, when aligned with a polypeptide according to SEQ ID NO: 1, comprises at least one amino acid substitution resulting in Ser (S), Ala (A) or Leu (L) at position 246, Trp (W) at position 307, Leu (L) at position 345, Ile (I) at position 365, and/or Phe (F) at position 534, wherein Ala at position 1 in SEQ ID NO: 1 is counted as number 1.

A polypeptide having lipase activity may be a polypeptide, which, when aligned with a polypeptide according to SEQ ID NO: 1, comprises at least one amino acid substitution resulting in Leu (L) at position 345 and/or Phe (F) at position 534, wherein Ala at position 1 in SEQ ID NO: 1 is counted as number 1.

A polypeptide having lipase activity as disclosed herein may comprise an amino acid sequence according to SEQ ID NO:1, wherein SEQ ID NO: 1 comprises at least one amino acid substitution P246A, P246L, P246S, L307W, F345L, S365I, and/or V534F.

A polypeptide having lipase activity may be a polypeptide, which when aligned with a polypeptide according to SEQ ID NO: 1, comprises at least one amino acid substitution resulting in Leu (L) at position 345 and/or Phe (F) at position 534, wherein Ala at position 1 in SEQ ID NO: 1 is counted as number 1.

A polypeptide having lipase activity as disclosed herein may comprise a polypeptide according to SEQ ID NO:1, wherein SEQ ID NO: 1 comprises at least one amino acid substitution S365I and/or V534F.

A polypeptide having lipase activity as disclosed herein may comprise a mature amino acid sequence of SEQ ID NO:1. The mature amino acid sequence of SEQ ID NO: 1 comprises amino acids 1 to 534 of SEQ ID NO:1.

As disclosed herein within the experimental part, some of the polypeptides/variants are particularly advantageous because—when compared to LIP1 wildtype—have an improved specificity towards short chain fatty acids (C4:0 and C6:0) and have a fatty acid profile which is comparable to the profiles of commercial animal lipases. The invention therefore provides a polypeptide having lipase activity wherein the polypeptide is a variant of SEQ ID NO: 1 and at least comprises one amino acid substitution resulting in Trp (W) at position 307, wherein Ala (A) at position 1 in SEQ ID NO: 1 is counted as number 1, wherein said variant has at least 80%, 85%, 90%, 91%, 92%, 93%, 94%, 95%, 96%, 97%, 98%% or 99% identity to amino acid sequence of SEQ ID NO: 1 and wherein said variant has a higher specific towards butyrate as a side chain than the specificity towards octanoate and/or palmitate as a side chain.

a polypeptide having lipase activity wherein the polypeptide is a variant of SEQ ID NO: 1 and at least comprises one amino acid substitution resulting in Leu (L) at position 345, wherein Ala (A) at position 1 in SEQ ID NO: 1 is counted as number 1, wherein said variant has at least 80%, 85%, 90%, 91%, 92%, 93%, 94%, 95%, 96%, 97%, 98%% or 99% identity to amino acid sequence of SEQ ID NO: 1 and wherein said variant has a higher specific towards butyrate as a side chain than the specificity towards octanoate and/or palmitate as a side chain.

a polypeptide having lipase activity wherein the polypeptide is a variant of SEQ ID NO: 1 and at least comprises one amino acid substitution resulting in Phe (F) at position 534, wherein Ala (A) at position 1 in SEQ ID NO: 1 is counted as number 1, wherein said variant has at least 80%, 85%, 90%, 91%, 92%, 93%, 94%, 95%, 96%, 97%, 98%% or 99% identity to amino acid sequence of SEQ ID NO: 1 and wherein said variant has a higher specific towards butyrate as a side chain than the specificity towards octanoate and/or palmitate as a side chain.

a polypeptide having lipase activity wherein the polypeptide is a variant of SEQ ID NO: 1 and at least comprises one amino acid substitution resulting in Ile (I) at position 365, wherein Ala (A) at position 1 in SEQ ID NO: 1 is counted as number 1, wherein said variant has at least 80%, 85%, 90%, 91%, 92%, 93%, 94%, 95%, 96%, 97%, 98%% or 99% identity to amino acid sequence of SEQ ID NO: 1 and wherein said variant has a higher specific towards butyrate as a side chain than the specificity towards octanoate and/or palmitate as a side chain.

Preferably, said variant has a higher specific towards butyrate as a side chain than the specificity towards palmitate as a side chain. The invention therefore provides a polypeptide having lipase activity wherein the polypeptide is a variant of SEQ ID NO: 1 and at least comprises one amino acid substitution resulting in Trp (W) at position 307, wherein Ala (A) at position 1 in SEQ ID NO: 1 is counted as number 1, wherein said variant has at least 80%, 85%, 90%, 91%, 92%, 93%, 94%, 95%, 96%, 97%, 98%% or 99% identity to amino acid sequence of SEQ ID NO: 1 and wherein said variant has a higher specific towards butyrate as a side chain than the specificity towards palmitate as a side chain.

a polypeptide having lipase activity wherein the polypeptide is a variant of SEQ ID NO: 1 and at least comprises one amino acid substitution resulting in Leu (L) at position 345, wherein Ala (A) at position 1 in SEQ ID NO: 1 is counted as number 1, wherein said variant has at least 80%, 85%, 90%, 91%, 92%, 93%, 94%, 95%, 96%, 97%, 98%% or 99% identity to amino acid sequence of SEQ ID NO: 1 and wherein said variant has a higher specific towards butyrate as a side chain than the specificity towards palmitate as a side chain.

a polypeptide having lipase activity wherein the polypeptide is a variant of SEQ ID NO: 1 and at least comprises one amino acid substitution resulting in Phe (F) at position 534, wherein Ala (A) at position 1 in SEQ ID NO: 1 is counted as number 1, wherein said variant has at least 80%, 85%, 90%, 91%, 92%, 93%, 94%, 95%, 96%, 97%, 98%% or 99% identity to amino acid sequence of SEQ ID NO: 1 and wherein said variant has a higher specific towards butyrate as a side chain than the specificity towards palmitate as a side chain.
a polypeptide having lipase activity wherein the polypeptide is a variant of SEQ ID NO: 1 and at least comprises one amino acid substitution resulting in Ile (I) at position 365, wherein Ala (A) at position 1 in SEQ ID NO: 1 is counted as number 1, wherein said variant has at least 80%, 85%, 90%, 91%, 92%, 93%, 94%, 95%, 96%, 97%, 98%% or 99% identity to amino acid sequence of SEQ ID NO: 1 and wherein said variant has a higher specific towards butyrate as a side chain than the specificity towards palmitate as a side chain.

The inventors of the present application have tested different substitutions at positions 307, 345, 534 and 365. Surprisingly, not all tested substitutions resulted in a preference for short chain fatty acids (C4, C6) compared to long chain fatty acids (C8 and higher), i.e. not all substitutions resulted in an improved of the wildtype lipase (SEQ ID NO: 1) and/or are not very active anymore. For example, for position 307 substitution to similar large amino acids M and F did not yield the required selectivity. For position 365: substitution to similar large amino acids Y, F, V, M and I did not yield the required selectivity. And for position 534: substitution to large amino acids L, M and I did also not yield the required selectivity.

Those positions in a polypeptide as disclosed herein, which may be a recombinant, synthetic or variant polypeptide, which correspond to the positions set out above in SEQ ID NO: 1 may be identified by aligning the sequence of the polypeptide of the present invention with that of SEQ ID NO: 1 using, for example, the alignment by the program Needle, to the most homologous sequence found by the Needle program (see above for details of this program). The positions in the polypeptide of the present disclosure corresponding to the positions in SEQ ID NO: 1 as set out above may thus be identified and are referred to as those positions defined with reference to SEQ ID NO: 1.

A polypeptide as disclosed herein may have a higher specificity towards butyrate than the specificity towards octanoate and/or palmitate. It is advantageous that when the ratio of butyrate to palmitate and/or the ratio of butyrate to octanoate is high, the lipase activity of a polypeptide as disclosed herein is still sufficient.

A polypeptide according to the present invention may be derived from any suitable eukaryotic or prokaryotic cell. A eukaryotic cell may be a mammalian, insect, plant, fungal, or algal cell. A prokaryotic cell may be a bacterial cell.

The wording "derived" or "derivable from" with respect to the origin of a polypeptide as disclosed herein, means that when carrying out a BLAST search with a polypeptide according to the present invention, the polypeptide according to the present invention may be derivable from a natural source, such as a microbial cell, of which an endogenous polypeptide shows the highest percentage homology or identity with the polypeptide as disclosed herein A polypeptide having lipase activity may be derived from any suitable fungi such as from *Aspergillus, Rhizomucor, Rhizopus*, or *Penicillium*, for instance *Aspergillus niger, A. oryzae, Rhizomucor meihei, Rhizopus microsporus*, or *Penicillium chrysogenum*. A polypeptide having lipase activity may also be derived from yeasts, such as *Candida, Kluyveromyces, Pichia*, or *Saccharomyces*, for instance *Candida rugosa, Kluyveromyces lactis, Pichia pastoris*, or *Saccharomyces cerevisiae*. A polypeptide having lipase activity may be derived from *Candida rugosa*.

A polypeptide according to the present invention may be a naturally occurring polypeptide or a genetically modified or recombinant polypeptide.

A polypeptide having lipase activity as disclosed herein may be an isolated, substantially pure, pure, recombinant, synthetic or variant polypeptide.

A polypeptide as disclosed herein may be purified. Purification of protein is known to a person skilled in the art. A well-known method for purification of proteins is high performance liquid chromatography.

A polypeptide as disclosed herein may be a variant of the mature polypeptide of SEQ ID NO:1 comprising at least one amino acid substitution resulting in Ser (S), Ala (A) or Leu (L) at position 246, Trp (W) at position 307, Leu (L) at position 345, Ile (I) at position 365, and/or Phe (F) at position 534, wherein Ala (A) at position 1 in SEQ ID NO: 1 is counted as number 1, and further having 1, 2, 3, 4, 5, 6, 7, 8, 9, 10, 11 or 12 or further amino substitutions, deletions and/or insertions, whereby the polypeptide still has the activity or function of the polypeptide disclosed herein. The skilled person will appreciate that these minor amino acid changes in the polypeptide disclosed herein may be present (for example naturally occurring mutations) or made (for example using r-DNA technology) without loss of the protein function or activity. In case these mutations are present in a binding domain, active site, or other functional domain of the polypeptide a property of the polypeptide may change but the polypeptide may keep its activity. In case a mutation is present which is not close to the active site, binding domain, or other functional domain, less effect may be expected.

The present disclosure features a biologically active fragment of a polypeptide as disclosed herein.

Biologically active fragments of a polypeptide of the invention include polypeptides comprising amino acid sequences sufficiently identical to or derived from the amino acid sequence of the lipase protein (e.g. the mature amino acid sequence of SEQ ID NO:1, which include fewer amino acids than the full-length protein but which exhibits at least one biological activity of the corresponding full-length protein. Typically, biologically active fragments comprise a domain or motif with at least one activity of the lipase protein. A biologically active fragment may for instance comprise a catalytic domain. A biologically active fragment of a protein of the invention can be a polypeptide which is, for example, 10, 25, 50, 100 or more amino acids in length. Moreover, other biologically active portions, in which other regions of the protein are deleted, can be prepared by recombinant techniques and evaluated for one or more of the biological activities of the native form of a polypeptide of the invention.

A polypeptide according to the present invention may be a fusion protein. Techniques for producing fusion polypeptides are known in the art, and include ligating the coding sequences encoding the polypeptides so that they are in frame. Expression of the fused polypeptide is under control of the same promoter (s) and terminator. The hybrid polypeptides may comprise a combination of partial or complete polypeptide sequences obtained from at least two different polypeptides wherein one or more may be heterologous to a host cell. Such fusion polypeptides from at least two different polypeptides may comprise a binding domain from one polypeptide, operably linked to a catalytic domain from a second polypeptide. Examples of fusion polypeptides and signal sequence fusions are for example as described in WO2010/121933, WO2013/007820 and WO2013/007821.

In one aspect, the present disclosure relates to a composition comprising a polypeptide having lipase activity as disclosed herein.

A composition as disclosed herein, may comprise a carrier, an excipient, an auxiliary enzyme, or other compounds. Typically, a composition, or a formulation, comprises a compound with which a lipase may be formulated.

An excipient as used herein may be an inactive substance formulated alongside with a polypeptide as disclosed herein, for instance sucrose or lactose, glycerol, sorbitol or sodium chloride. A composition comprising a polypeptide as disclosed herein may be a liquid composition or a solid composition. A liquid composition usually comprises water. When formulated as a liquid composition, the composition usually comprises components that lower the water activity, such as glycerol, sorbitol or sodium chloride (NaCl). A solid composition comprising a polypeptide as disclosed herein may comprise a granulate comprising the enzyme or the composition comprises an encapsulated polypeptide in liquid matrices like liposomes or gels like alginate or carrageenans. There are many techniques known in the art to encapsulate or granulate a polypeptide or enzyme (see for instance G. M. H. Meesters, "Encapsulation of Enzymes and Peptides", Chapter 9, in N. J. Zuidam and V. A. Nedović (eds.) "Encapsulation Technologies for Active Food Ingredients and food processing" 2010).

A composition as disclosed herein may also comprise a carrier comprising a polypeptide as disclosed herein. A polypeptide as disclosed herein may be bound or immobilized to a carrier by known technologies in the art.

Disclosed herein is also a process for preparing a composition comprising a polypeptide as disclosed herein, which may comprise spray drying a fermentation medium comprising the polypeptide, or granulating, or encapsulating a polypeptide as disclosed herein, and preparing the composition.

The present disclosure also relates to a packaging, such as a can, a keg or a barrel comprising a polypeptide or a composition comprising a polypeptide as disclosed herein.

Polypeptides having a lipase activity as disclosed herein may be obtained by several procedures known to a skilled person in the art, such as:
1. Error prone PCR to introduce random mutations, followed by a screening of obtained (variant) polypeptides and isolating of (variant) polypeptide(s) with improved kinetic properties
2. Family shuffling of related variants of the genes encoding the polypeptide according to the invention, followed by a screening of obtained variants and isolating of variants with improved kinetic properties Variants of genes encoding a polypeptide of the present invention leading to an increased level of mRNA and/or protein, resulting in more activity may be obtained by modifying the polynucleotide sequences of said genes. Among such modifications are included:
1. Improving the codon usage in such a way that the codons are (optimally) adapted to the parent microbial host.
2. Improving the codon pair usage in such a way that the codons are (optimally) adapted to the parent microbial host
3. Addition of stabilizing sequences to the genomic information encoding a polypeptide according to the invention resulting in mRNA molecules with an increased half life Methods to isolate variants with improved catalytic properties or increased levels of mRNA or protein are described in WO03/010183 and WO03/01311. Methods to optimize the codon usage in parent microbial strains are for instance described in WO2008/000632. Methods for the addition of stabilizing elements to the genes encoding the polypeptide of the invention are described in WO2005/059149.

Generating a variant polypeptide as disclosed herein may include expressing a gene encoding the variant polypeptide in a suitable (recombinant) host cell, and cultivating the host cell to generate the variant polypeptide.

Accordingly, in one aspect the present disclosure relates to a method for generating a variant polypeptide wherein the method comprises
a. selecting a parent polypeptide comprising at least 80%, 85%, 90%, 91%, 92%, 93%, 94%, 95%, 96%, 97%, 98%, 99% or 100% identity to the amino acid sequence according to SEQ ID NO: 1; and,
b. substituting at least one amino acid into Ser (S), Ala (A) or Leu (L) at position 246, Trp (W) at position 307, Leu (L) at position 345, Ile (I) at position 365, and/or Phe (F) at position 534, wherein said position is defined with reference to SEQ ID NO: 1, wherein Ala (A) at position 1 in SEQ ID NO: 1 is counted as number 1; and
c. generating the variant polypeptide, wherein the polypeptide having lipase activity has a higher specificity towards butyrate than the specificity towards octanoate and/or palmitate.

Generating a variant polypeptide in a method as disclosed herein may further comprise modifying a host cell such that a variant polypeptide is expressed by the host cell and cultivating the host cell in a suitable fermentation medium. Modifying and cultivating a host cell can be performed by standard methods known to a person skilled in the art.

In another aspect the present disclosure relates to a nucleic acid encoding a lipase, which has at least 80%, 85%, 90%, 95%, 96%, 97%, 98%, or 99% sequence identity to SEQ ID NO: 2, wherein SEQ ID NO: 2 comprises at least one mutation resulting in Ser (S), Ala (A) or Leu (L) at position 246, Trp (W) at position 307, Leu (L) at position 345, Ile (I) at position 365, and/or Phe (F) at position 534, wherein the position is defined with reference to SEQ ID NO: 1, wherein alanine at position 1 in SEQ ID NO: 1 is counted as number 1.

Sequence identity of a nucleic acid disclosed herein may be determined to the full length nucleic acid sequence of SEQ ID NO:2.

Typically, a polynucleotide sequence as disclosed herein is codon optimized, or a codon pair optimized sequence for optimal expression of a polypeptide as disclosed herein in a particular host cell.

In one embodiment, a nucleic acid is disclosed that is an isolated, substantially pure, pure, recombinant, synthetic or variant nucleic acid of the nucleic acid as disclosed herein.

In another embodiment, a nucleic acid molecule of the invention comprises a nucleic acid molecule which is the reverse complement of the nucleotide sequence shown in SEQ ID NO: 2, or the reverse complement of the mature coding sequence of SEQ ID NO: 2.

Also disclosed is a nucleic acid that hybridizes under medium stringency, preferably under high stringency conditions to the complementary strand of the mature polypeptide coding sequence of SEQ ID NO:2.

A nucleic acid molecule which is complementary to another nucleotide sequence is one which is sufficiently complementary to the other nucleotide sequence such that it can hybridize to the other nucleotide sequence thereby forming a stable duplex. The term "cDNA" (complementary DNA) is defined herein as a DNA molecule which can be prepared by reverse transcription from a mRNA molecule. In prokaryotes the mRNA molecule is obtained from the transcription of the genomic DNA of a gene present in a cell. In eukaryotic cells genes contain both exons, i.e. coding sequences, and introns, i.e. intervening sequences located between the exons. Therefore, in eukaryotic cells the initial, primary RNA obtained from transcription of the genomic DNA of a gene is processed through a series of steps before appearing as mRNA. These steps include the removal of intron sequences by a process called splicing. cDNA derived from mRNA only contains coding sequences and can be directly translated into the corresponding polypeptide product.

The present disclosure also features nucleic acid fragments which encode the above biologically active fragments of the lipase protein.

In another aspect, the present disclosure relates to an expression vector comprising a nucleic acid as disclosed herein operably linked to at least one control sequence that direct expression of the polypeptide in a host cell.

There are several ways of inserting a nucleic acid into a nucleic acid construct or an expression vector which are known to a skilled person in the art, see for instance Sambrook & Russell, *Molecular Cloning: A Laboratory Manual*, 3rd Ed., CSHL Press, Cold Spring Harbor, N.Y., 2001. It may be desirable to manipulate a nucleic acid encoding a polypeptide of the present invention with control sequences, such as promoter and terminator sequences.

A promoter may be any appropriate promoter sequence suitable for a eukaryotic or prokaryotic host cell, which shows transcriptional activity, including mutant, truncated, and hybrid promoters, and may be obtained from polynucleotides encoding extracellular or intracellular polypeptides either endogenous (native) or heterologous (foreign) to the cell. The promoter may be a constitutive or inducible promoter. A promoter may be an inducible promoter, for instance a starch inducible promoter.

Strong constitutive promoters are well known and an appropriate one may be selected according to the specific sequence to be controlled in the host cell.

Suitable inducible promoters useful in bacteria, such as Bacilli, include promoters from Gram-positive microorganisms such as, but are not limited to, SP01-26, SP01-15, veg, pyc (pyruvate carboxylase promoter), and amyE. Examples of promoters from Gram-negative microorganisms include, but are not limited to, tac, tet, trp-tet, lpp, lac, lpp-lac, laclq, T7, T5, T3, gal, trc, ara, SP6, I-P$_R$, and I-P$_L$.

Additional examples of promoters useful in bacterial cells, such as Bacilli, include the α-amylase and SPo2 promoters as well as promoters from extracellular protease genes.

Promoters suitable in filamentous fungi are promoters which may be selected from the group, which includes but is not limited to promoters obtained from the polynucleotides encoding *A. oryzae* TAKA amylase, *Rhizomucor miehei* aspartic proteinase, *Aspergillus* gpdA promoter, *A. niger* neutral alpha-amylase, *A. niger* acid stable alpha-amylase, *A. niger* or *A. awamori* glucoamylase (glaA), *A. niger* or *A. awamori* endoxylanase (xlnA) or beta-xylosidase (xlnD), *T. reesei* cellobiohydrolase I (CBHI), *R. miehei* lipase, *A. oryzae* alkaline protease, *A. oryzae* triose phosphate isomerase, *A. nidulans* acetamidase, *Fusarium venenatum* amyloglucosidase (WO 00/56900), *Fusarium venenatum* Dania (WO 00/56900), *Fusarium venenatum* Quinn (WO 00/56900), *Fusarium oxysporum* trypsin-like protease (WO 96/00787), *Trichoderma reesei* beta-glucosidase, *Trichoderma reesei* cellobiohydrolase I, *Trichoderma reesei* cellobiohydrolase II, *Trichoderma reesei* endoglucanase I, *Trichoderma reesei* endoglucanase II, *Trichoderma reesei* endoglucanase III, *Trichoderma reesei* endoglucanase IV, *Trichoderma reesei* endoglucanase V, *Trichoderma reesei* xylanase I, *Trichoderma reesei* xylanase II, *Trichoderma reesei* beta-xylosidase, as well as the NA2-tpi promoter (a hybrid of the promoters from the polynucleotides encoding *A. niger* neutral alpha-amylase and *A. oryzae* triose phosphate isomerase), and mutant, truncated, and hybrid promoters thereof.

Promoters which can be used in yeasts include e.g. promoters from glycolytic genes, such as the phosphofructokinase (PFK), triose phosphate isomerase (TPI), glyceraldehyde-3-phosphate dehydrogenase (GPD, TDH3 or GAPDH), pyruvate kinase (PYK), phosphoglycerate kinase (PGK) promoters from yeasts or filamentous fungi; more details about such promoters from yeast may be found in (WO 93/03159). Other useful promoters are ribosomal protein encoding gene promoters, the lactase gene promoter (LAC4), alcohol dehydrogenase promoters (ADHI, ADH4, and the like), and the enolase promoter (ENO). Other promoters, both constitutive and inducible, and enhancers or upstream activating sequences will be known to those of skill in the art. The promoters used in the host cells of the invention may be modified, if desired, to affect their control characteristics. Suitable promoters in this context include both constitutive and inducible natural promoters as well as engineered promoters, which are well known to the person skilled in the art. Suitable promoters in eukaryotic host cells may be GAL7, GAL10, or GAL1, CYC1, HIS3, ADH1, PGL, PH05, GAPDH, ADC1, TRP1, URA3, LEU2, ENO1, TPI1, and AOX1. Other suitable promoters include PDC1, GPD1, PGK1, TEF1, and TDH3. Examples of carbohydrate inducible promoters which can be used are GAL promoters, such as GAL1 or GAL10 promoters.

Any terminator which is functional in a cell as disclosed herein may be used, which are known to a person skilled in the art. Examples of suitable terminator sequences in filamentous fungi include terminator sequences of a filamentous fungal gene, such as from *Aspergillus* genes, for instance from the gene *A. oryzae* TAKA amylase, the genes encoding *A. niger* glucoamylase (glaA), *A. nidulans* anthranilate synthase, *A. niger* alpha-glucosidase, trpC and/or *Fusarium oxysporum* trypsin-like protease.

In another aspect, the present invention relates to a host cell comprising a nucleic acid construct or an expression vector as disclosed herein. A suitable host cell may be a mammalian, insect, plant, fungal, or algal cell, or a bacterial cell. A suitable host cell may be a fungal cell, for instance from the genus *Acremonium, Aspergillus, Chrysosporium, Fusarium, Myceliophthora, Penicillium, Rasamsonia, Talaromyces, Thielavia, Trichoderma, Saccaromyces, Kluyveromyces, Pichia*, for instance *Aspergillus niger, Aspergillus awamori, Aspergillus foetidus, A. oryzae, A. sojae, Talaromyces emersonii, Rasamsonia emersonii Chrysosporium lucknowense, Fusarium oxysporum, Myceliophthora thermophila, Thielavia terrestris* or *Trichoderma reesei* or, *Saccharomyces cerevisiae, Kluyveromyces lactis, Pichia pastoris*. A host cell may be a *Pichia pastoris* host cell.

Suitable bacterial host cells may be from the genus *Bacillus* or *Escherichia, Streptomyces*, or *Pseudomonas*, for instance from the species *Bacillus alkalophilus, Bacillus amyloliquefaciens, Bacillus brevis, Bacillus circulans, Bacillus clausii, Bacillus coagulans, Bacillus firmus, Bacillus lautus, Bacillus lentus, Bacillus licheniformis, Bacillus megaterium, Bacillus pumilus, Bacillus stearothermophilus,*

*Bacillus subtilis,* or *Bacillus thuringiensis;* or a *Streptomyces lividans* or *Streptomyces murinus; E. coli.*

A host cell may be a recombinant or transgenic host cell. The host cell may be genetically modified with a nucleic acid construct or expression vector as disclosed herein with standard techniques known in the art, such as electroporation, protoplast transformation or conjugation for instance as disclosed in Sambrook & Russell, *Molecular Cloning: A Laboratory Manual,* 3rd Ed., CSHL Press, Cold Spring Harbor, N.Y., 2001. A recombinant host cell may overexpress a polypeptide according to the present disclosure by known techniques in the art.

In one aspect, the present disclosure relates to a method for preparing a polypeptide having a lipase activity as disclosed herein comprising cultivating a recombinant host cell in a suitable fermentation medium under conditions that allow expression of the polypeptide. A skilled person in the art understands how to perform a process for the production of a polypeptide as disclosed herein depending on a host cell used, such as pH, temperature and composition of a fermentation medium. Usually a fermentation medium comprises a carbon and nitrogen source for growth of the host cell and production of a polypeptide as disclosed herein. A fermentation medium may further comprise an inducer for producing a lipase as disclosed herein. Host cells can be cultivated in shake flasks, or in fermenters having a volume of 0.5 or 1 litre or larger to 10 to 100 or more cubic metres. Cultivation may be performed aerobically or anaerobically depending on the requirements of a host cell.

Preparing a polypeptide as disclosed herein comprises recovering or isolating a polypeptide as disclosed herein from the fermentation medium. Recovering or isolating a polypeptide from a fermentation medium may for instance be performed by centrifugation, filtration, and/or ultrafiltration. Recovering or isolating may further comprise a step of chromatography.

In another aspect, the present disclosure relates to a process for preparing a product comprising a lipid comprising bringing the lipid into contact with a polypeptide having a lipase activity, or a composition comprising a polypeptide as disclosed herein.

A product comprising a lipid may be a food product comprising a lipid, for instance a dairy product such as cheese.

Preparing a product comprising a lipid, such as a food product, may be performed according to any suitable way known to a person skilled in the art. For instance, a process for making a food product such as cheese typically comprises separating milk into solid curds an liquid whey. Bringing a lipid into contact with a polypeptide as disclosed herein may comprise bringing curd into contact with a polypeptide as disclosed herein.

Bringing a lipid into contact with a polypeptide or a composition comprising a polypeptide as disclosed herein, may comprise incubating the polypeptide with an intermediate form of a product comprising a lipid at a suitable temperature and/or during a suitable period of time. Incubating may comprise adding a polypeptide as disclosed to an intermediate form of a product comprising a lipid.

A process for preparing a food product may comprise a step of pasteurizing or sterilizing a food product or an intermediate form of a food product.

Pasteurizing a food product or an intermediate form of a food product may be performed by any suitable process known in the art. For instance, pasteurizing comprises bringing a food product or an intermediate form of a food product to a temperature of between 60 and 65 degrees Celsius during a period of between 5 to 30 min, such as for instance between 10 and 20 min, or to a temperature of between 70 and 75 degrees Celsius for 5 to 30 seconds.

Sterilizing a food product or an intermediate form of a food product may be performed by any suitable process known in the art. Sterilizing may comprise bringing a food product or an intermediate form of a food product to a temperature of between 80 and 100 degrees Celsius during 5 to 40 min. Sterilization may also be performed ultra-high temperature (UHT) sterilization, which comprises bringing a food product or an intermediate form of a food product to a temperature of between 110 and 140 degrees Celsius during 1 to 5 seconds.

A food product that may be prepared in a process as disclosed herein may be a dairy product, for instance butter, cream, or cheese, or any suitable food product comprising a dairy product.

In the event the food product is cheese, an intermediate form of the food product may be milk, or curd.

The present disclosure also relates to a product comprising a lipid, for instance a food product, obtainable by a process as disclosed herein.

In one aspect, the present disclosure relates to the use of a polypeptide having lipase activity as disclosed herein for improving flavour of a product comprising a lipid.

The present disclosure also provides a process for improving flavour of a composition comprising a lipid, comprising incubating the composition comprising a lipid with a polypeptide as disclosed herein.

A composition comprising a lipid may for instance be a food product comprising a lipid as disclosed herein above. Improving flavour of a product comprising a lipid as used herein comprises reducing a soapy flavour of a product comprising a lipid. For instance, improving flavour of a product comprising a lipid comprises reducing formation of long chain fatty acids such as fatty acids having at least 8 carbon atoms, for instance octanoate and/or palmitate as compared to the use of a polypeptide comprising an amino acid sequence of SEQ ID NO: 1, such an amino acid sequence according to SEQ ID NO: 1 which does not comprise an amino acid substitution resulting in Ser (S), Ala (A) or Leu (L) at position 246, Trp (W) at position 307, Leu (L) at position 345, Ile (I) at position 365, and/or Phe (F) at position 534, wherein the substitution is defined with reference to SEQ ID NO: 1, wherein Ala(A) at position 1 in SEQ ID NO: 1 is counted as number 1.

A use of a polypeptide having a lipase activity for improving flavour, or a process for improving flavour as disclosed as disclosed here comprises incubating a lipid as disclosed herein above.

The following examples illustrate the invention.

EXAMPLES

Materials and Methods

Strains
*Pichia pastoris* (*Komagataella phaffii*) (strain ATCC 76273/CBS 7435/CECT 11047/NRRL Y-11430/Wegner 21-1) was used (Cregg J M, Barringer K J, Hessler A Y and Madden K R (1985). *Pichia pastoris* as a host system for transformations. Mol. Cell. Biol., 5, 3376-3385).
Molecular Biology Techniques
Molecular biology techniques were performed according to Sambrook & Russell, Molecular Cloning: A Laboratory Manual, 3rd Ed., CSHL Press, Cold Spring Harbor, N.Y., 2001. PCR is disclosed in for example Innes et al. (1990)

PCR protocols, a guide to methods and applications, Academic Press, San Diego. Polymerase chain reaction (PCR) was performed on a thermocycler with Phusion High-Fidelity DNA polymerase (Finnzymes OY, Aspoo, Finland) according to the instructions of the manufacturer.

Example 1

1.1. Preparation of Histidine Auxotrophic *Pichia pastoris* (*Komagataella Phaffii*) Strain The HIS4 gene (SEQ ID NO: 3) from *Komagataella phaffii* strain ATCC 76273 was deleted by using a FLP recombinase and two asymmetric FLP recombination target sequences (FRTs) derived from *S. cerevisiae* 2 µm circle (Som, T., Armstrong, K. A., Volkert, F. C., and Broach, J. R. (1988), Cell 52: p. 27-37; Broach, J. R. (1981) The yeast plasmid 2 µm circle. In: The molecular biology of the yeast *Saccharomyces*: Life cycle and inheritance. Strathern, J. N., Jones, E. W., and Broach, J. R. (eds)., Cold Spring Harbor, pp. 455-470). This resulted in a histidine auxotrophic strain DSM101A wherein the 2682 bp HIS4 open reading frame (SEQ ID NO: 3) was replaced with a 34 bp FRT recombination site (SEQ ID NO: 4). The HIS4 deletion was confirmed by Southern analyses and phenotypically. The histidine auxotrophic strain DSM101A was not able to grow on MD media (Sambrook & Russell) without histidine, whereas this strain grew well on MD media with histidine (40 µg/ml).

MD contains 15 g/L agar, 800 mL H$_2$O, after autoclaving the following filter sterilized solutions were added: 100 mL 10×YNB (134 g/L Difco™ Yeast Nitrogen Base w/o Amino Acids), 2 mL 500×B (0.02% D-Biotin), 100 mL 10×D (220 g/L α-D(+)-Glucose monohydrate).

1.2. Preparation of Variant Lipase DNA Construct

The *Pichia* expression vector pD902 (DNA2.0, CA, USA) was used for expression of mature *Candida rugosa* 534 lipase polypeptide variants (variants of amino acids 1-534 of SEQ ID NO: 1). The lipase encoding sequences were fused behind the α-mating factor from *S. cerevisiae* followed by a Kex2 processing site composed of Lysine, Arginine (KR) and a Glutamine Alanine repeat (EAEA) (SEQ ID NO: 5) The genes were placed under control of the methanol inducible AOX1 promoter as described previously (Brocca S., Schmidt-Dannert C., Lotti M., Alberghina L., Schmid R. D., Protein Sci. 1998(6):1415-1422) and WO9914338A1. The *Candida rugosa* 534 wild type lipase polypeptide sequence (SEQ ID NO: 1) was used to design a nucleotide sequence encoding the lipase with a codon usage that matched the coding usage of *Pichia pastoris* (SEQ ID NO: 2). Additionally, a XhoI site was placed at the 5' end and a NotI site at the 3' end. The nucleotide sequence comprising the codon optimized gene fragment encoding the *Candida rugosa* 534 wild type sequence (LIP1), the α-mating factor from *S. cerevisiae* followed by a Kex2 processing site composed of Lysine, Arginine (KR) and a Glutamine Alanine repeat (EAEA) and a XhoI site at the 5' end and a NotI site at the 3' end is shown in SEQ ID NO: 7. The pD902 vector with SEQ ID NO: 7 is depicted in FIG. 1.

Variants of the LIP1 protein (SEQ ID NO:1) were made with the amino acid substitutions P246A, P246F, P246L, P246S, L307W, F345L, S365I, S365L, L410W or V534F. Positions of the amino acid change are indicated in comparison with SEQ ID NO: 1.

The LIP1 encoding gene variants containing the amino acid substitution P246A, P246F, P246L, P246S, L307W, F345L, S365I, S365L, L410W or V534F were cloned into vector pD902 following the procedure as described above for the LIP1 encoding wild type sequence. The pD902 vectors containing the lip1 gene variants were digested by SacI and transformed to *Pichia pastoris* strain DSM101A. Transformation procedure was performed according to condensed electroporation protocol using freshly prepared solutions (Lin-Cereghino J1, Wong W W, Xiong S, Giang W, Luong L T, Vu J, Johnson S D, Lin-Cereghino G P. Biotechniques. (2005) 38, (1):44-48). Transformants were plated on YPDS agar plates with 500 µg/mL Zeocin (YPDS: 1% yeast extract, 2% peptone, 2% glucose, 1M sorbitol, 2% agar) and incubated at 30° C. for 72 h.

Example 2. Production of Lipase Variants

Histidine auxotrophic *Pichia pastoris* clones containing a LIP1 variant with amino acid substitution P246A, P246F, P246L, P246S, L307W, F345L, S365I, S365L, L410W or V534F were cultured in 1.5 mL BMD 1% medium (0.2M Potassium Phosphate buffer, 13.4 g/l Yeast Nitrogen Base, 0.4 mg/ml biotin, 1.1% w/v glucose, filter sterilized) in 24 deep wells plates (Axygen, Calif., USA). These cultures were incubated for 60 hours at 28° C., 550 rpm (Microton incubator shaker (Infors AG, Bottmingen, Switzerland). After 60 hours of incubation, 1.25 mL BMM2 (0.2 M Potassium Phosphate buffer, 13.4 g/l Yeast Nitrogen Base, 0.4 mg/ml Biotin, 1% methanol, filter sterilized) was added and growth was continued at 28° C., 550 rpm. After 8 hours, 250 µL BMM10 (0.2 M Potassium Phosphate buffer, 13.4 g/l Yeast Nitrogen Base, 0.4 mg/ml Biotin, 5% methanol, filter sterilized) was added to induce lipase production. Addition of 250 µL BMM10 was repeated after 24 hours, 48 hours and 72 hours after the first addition. 12 hours after the last addition of BMM10, the cultures were centrifuged (5 min, 1000 g) and supernatants were harvested and stored at −20° C.

Example 3. Lipase Activity on p-NP Substrates

The activity of the LIP1 variants P246A, P246F, P246L, P246S, L307W, F345L, S365I, S365L, L410W and V534F was determined in assays using the chromogenic substrates: 4-nitrophenyl butyrate (Sigma N9874), 4-nitrophenyl octanoate (Sigma 21742) and 4-nitrophenyl palmitate (Sigma N2752). An 8.0 mM solution of the chromogenic substrate in 2-propanol was made. Subsequently, 3.5 mL of this solution was added to 46.5 mL 100 millimol/L sodium acetate buffer pH 4.5 containing 1% Triton X-100, under vigorously stirring. The enzyme reaction was started by mixing 20 µL of a suitable dilution of the supernatant prepared as described above with 180 µL substrate solution (substrate concentration during incubation is 0.5 mM) in a microtiter plate. During incubation at 25° C. in a TECAN Infinite M1000 micro titer plate reader, the change in absorption of the mixture was measured for 30 minutes at 348 nm (isosbestic point of 4-nitrophenol). The slope (deltaOD/min) of the linear part of the curve is used as measure for the activity.

The activity can be expressed as the amount of enzyme that liberates 1 micromol p-nitrophenol per minute under the conditions of the test. In Table 1, the activity is expressed as the amount of substrate released per ml of enzyme solution (per minute). Samples were diluted such to assure that the absorbance increase after 30 minutes is less than 1.0. Calibration is done using a 4-nitrophenol standard solution (Sigma N7660) diluted in the same buffer.

Table 1 shows the activity of Lip1 mutant lipase with a mutation P246A, P246F, P246L, P246S, L307W, F345L, S365I, S365L, L410W and V534F and the wild type Lip1 lipase on pNP-butyrate and pNP-palmitate. As a reference the activity of three commercial lipases from animal origin (Kerry kid lipase (batch GT00013178), Kerry Halal calf lipase (batch GT00012987) and Kerry lamb lipase (batch GT00012631 produced by DSM) were measured in the same way as described above. Table 1 shows that the ratio of the activities on butyrate versus palmitate of all mutant lipase enzymes was higher than the ratio of the activities of the wild-type lipase and the three animal lipases.

TABLE 1

Activity of LIP 1 variants and references samples on pNP-butyrate and pNP-palmitate as substrate measured at pH 4.5 and 25° C. and ratio of activities.

| Variant | pNP-butyrate (μmol/min · mL) | pNP-palmitate (μmol/min · mL) | Ratio pNP but/pal |
|---|---|---|---|
| L410W | 0.89 | 0.01 | 102.8 |
| V534F | 0.89 | 0.02 | 48.3 |
| S365I | 1.53 | 0.04 | 41.4 |
| S365L | 1.17 | 0.03 | 41.2 |
| F345L | 0.73 | 0.02 | 35.8 |
| L307W | 0.36 | 0.01 | 26.6 |
| P246S | 0.55 | 0.04 | 13.8 |
| P246F | 0.14 | 0.02 | 8.1 |
| P246L | 0.05 | 0.01 | 7.1 |
| P246A | 0.39 | 0.08 | 5.1 |
| Wild Type | 1.42 | 1.91 | 0.7 |

| reference | pNP-butyrate (μmol/min · g) | pNP-palmitate (μmol/min · g) | Ratio pNP but/pal |
|---|---|---|---|
| Lamb | 5.09 | 1.96 | 2.6 |
| Kid | 2.16 | 1.39 | 1.6 |
| Calf | 1.49 | 3.79 | 0.4 |

Table 2 shows the activity of Lip1 mutant lipase with a mutation P246A, P246F, P246L, P246S, L307W, F345L, S365I, S365L, L410W or V534F and the wild type Lip1 lipase on pNP-butyrate and pNP-palmitate. As a reference the activity of three commercial lipases from animal origin (Kerry kid lipase (batch GT00013178), Kerry Halal calf lipase (batch GT00012987) and Kerry lamb lipase (batch GT00012631) produced by DSM) were measured in the same way as described above.

Table 2 shows that the ratio of the activity on pNP-butyrate versus the activity on pNP-octanoate of five variants (L307W, P246S, P246F, P246L & P246A) was significantly higher than pNP-butyrate/pNP-octanoate ratio from the animal lipase.

TABLE 2

Activity of LIP 1 variants and references on pNP-butyrate and pNP-octanoate as substrate measured at pH 4.5 and 25° C. and ratio of activities.

| Variant | pNP-butyrate (μmol/min · mL) | pNP-octanoate (μmol/min · mL) | Ratio pNP but/oct |
|---|---|---|---|
| L410W | 2.25 | 3.84 | 0.6 |
| V534F | 2.37 | 5.37 | 0.4 |
| S365I | 3.42 | 6.24 | 0.5 |
| S365L | 3.03 | 3.44 | 0.9 |
| F345L | 1.04 | 1.95 | 0.5 |
| L307W | 0.61 | 0.02 | 29.4 |
| P246S | 1.19 | 0.04 | 33.7 |
| P246F | 0.31 | 0.02 | 17.5 |
| P246L | 0.12 | 0.00 | 78.0 |
| P246A | 0.78 | 0.02 | 34.9 |

TABLE 2-continued

Activity of LIP 1 variants and references on pNP-butyrate and pNP-octanoate as substrate measured at pH 4.5 and 25° C. and ratio of activities.

| reference | pNP-butyrate (μmol/min · g) | pNP-octanoate (μmol/min · g) | Ratio pNP but/pal |
|---|---|---|---|
| Lamb | 7.02 | 18.7 | 0.4 |
| Kid | 3.41 | 16.0 | 0.2 |
| Calf | 2.00 | 18.7 | 0.1 |

As mentioned earlier, the C4/C8 ratio is of less relevance. The more relevant ratio is the C4/C16 ratio.

Example 4. Lipase Activity on Triglycerides Via pH-Stat Technique

Lipase activity measurements were also performed on tributyrin and trioctanoin using a pH-Stat-unit consisting of TIM854 titrator Monoburette with pH 5.0 as set-point. Substrate solutions were prepared by dissolving 4.5 mM tributyrin (Sigma T8626) and trioctanoin (Sigma T9126) in 30 mL Triton X-100 at 35° C. Subsequently, 220 mL of 0.86 M NaCl solution was added. Before use, the pH of the solution was adjusted to pH 4.8 with a diluted HCL solution.

A double walled vessel kept at 37° C. was filled with 25 mL of substrate solution. The reaction was started by adding 50 μL of the supernatant prepared as described above. A solution of 0.010 M NaOH was used as titrant. The amount of sodium hydroxide, dosed per minute in order to keep the pH constant, is directly proportional to the amount of released free fatty acid and therefore a measure for the activity in the sample in μmol FFA/min. One unit of activity corresponds to the amount of enzyme that forms one micromole free fatty acids (FFA's) per minute under the conditions of the test.

Table 3 shows that the ratio of the lipase activity towards tributrate versus the activity on trioctanoate of five variants (V534F, F345L, L307W, P246S & P246F) was significantly higher than the tributyrin/trioctanoate ratio of the wild type LIP1 lipase. The tributyrin/trioctanoate ratio of animal lipase was in the same order of magnitude as the five mutant Lip1 lipases.

TABLE 3

Activity of LIP 1 variants and references on tributyrin and trioctanoin as a substrate measured at pH 5.0 and 37° C. and the ratio of activities.

| Variant | Tributyrin (μmol/min/mL) | Trioctanoin (μmol/min · mL) | Ratio tribut/triocta |
|---|---|---|---|
| L410W | 0.7 | 0.6 | 1.3 |
| V534F | 0.8 | 0.02 | 38 |
| S365I | 2.8 | 2.2 | 1.3 |
| S365L | 1.9 | 1.3 | 1.5 |
| F345L | 0.5 | 0.007 | 71 |
| L307W | 0.01 | 0.001 | 6.4 |
| P246S | 0.06 | 0.005 | 14 |
| P246F | 0.10 | 0.005 | 21 |
| P246L | 0.004 | 0.125 | 0.0 |
| P246A | 0.025 | 0.100 | 0.3 |
| WT LIP1 | 1.3 | 0.9 | 1.5 |

| reference | Tributyrin (μmol/min · g) | Trioctanoin (μmol/min · g) | Ratio tribut/triocta |
|---|---|---|---|
| Lamb | 208 | 5.5 | 38 |
| Kid | 174 | 1.7 | 105 |
| Calf | 106 | 1.5 | 70 |

Example 5: Production of Lipase Variants in Shake Flask

Histidine auxotrophic *Pichia pastoris* clones containing a LIP1 variant with amino acid substitution P246A, P246F, P246L, P246S, L307W, F345L, S365I, S365L, L410W or V534F were cultured in 20 mL BMDH 1% medium (0.2M Potassium Phosphate buffer pH 6.8, 13.4 g/l Yeast Nitrogen Base, 0.4 mg/ml biotin, 1.1% w/v glucose, 0.004% L-histidine, 0.02% Clerol FBA 3107K (filter sterilized) in 100 ml baffled shake flasks. These cultures were incubated for 60 hours at 28° C. and 250 rpm (INNOVA 4300 shaker). After 60 hours of incubation, methanol was added to 0.5% final concentration (with respect to starting volume) and growth was continued at 28° C. and 250 rpm to induce enzyme expression. Addition of methanol to 0.5% was repeated after 24 hours, 48 hours and 72 hours after the first addition. 24 hours after the last addition of methanol the cultures were centrifuged (5 min, 5000 g) and supernatants were stored at −20° C.

Example 6: Fatty Acid Specificity of LIP1 Variants Using Milk Cream as Substrate Substrate was prepared by diluting milk cream (fat content approximately 35% fat (w/w)) ten times with 1% triton X-100 solution. pH was adjusted to 5.5 by adding 0.1 M HCl solution. A mixture of 800 μL substrate and 100 μL of a suitable dilution of a supernatant of shake flask grown LIP1 variant, wild type LIP1 or reference sample was incubated overnight (approximately 16 h) in a 37° C. water bath with continuous mixing. A suitable dilution of the enzyme is the amount of enzyme that realizes a degree of hydrolysis of at least 1 mol % but not more than 50 mol %. After stopping the reaction by adding 100 μL 1 M HCl, the free fatty acid content was determined with gas chromatography (see Example 9).

Table 4 shows the fatty acid specificity of LIP1 mutant lipase with a mutation F345L, L307W, L410W, P246A, P246F, P246L, P246S, S365I, S365L or V534F and the wild type LIP1 lipase on milk cream as substrate. As a reference the specificity of three commercial lipases from animal origin (Kerry kid lipase (DSM batch GT00013178), Kerry Halal calf lipase (DSM batch GT00012987) and Kerry lamb lipase (DSM batch GT00012631) were measured in the same way as described above. When comparing with LIP1 wild type, the specificity towards short chain fatty acids (C4:0 and 06:0) was significantly improved for variant F345L, L307W, L410W, P246F, S365I, S365L and V534F. For these improved variants, the fatty acid profiles are comparable with the profiles of the commercial animal lipases that are currently in use for cheese application.

TABLE 4

Free fatty acid profiles (as mol %) of LIP1 variants and reference samples after overnight incubation in milk cream/triton X-100 emulsion at 37° C. and pH 5.5. Last column gives the total amount of free fatty acids formed in mmol/kg.

| Variant | C4:0 FFA | C6:0 FFA | C8:0 FFA | C10:0 FFA | C12:0 FFA | C14:0 FFA | C16:0 FFA | C16:1 FFA | C18:0 FFA | C18:1 FFA | Total FFA (mmol/kg) |
|---|---|---|---|---|---|---|---|---|---|---|---|
| F345L | 41.0 | 15.9 | 8.2 | 7.6 | 1.1 | 2.3 | 7.5 | 0.7 | 5.7 | 10.1 | 3.6 |
| L307W | 53.8 | 8.5 | 2.0 | 2.0 | 0.8 | 2.9 | 10.5 | 0.5 | 8.2 | 10.7 | 1.9 |
| L410W | 30.6 | 6.4 | 9.8 | 22.0 | 8.0 | 8.8 | 7.0 | 0.7 | 2.5 | 4.1 | 7.7 |
| P246A | 8.0 | 1.0 | 0.6 | 4.7 | 3.4 | 6.0 | 30.8 | 2.3 | 10.9 | 32.4 | 6.9 |
| P246F | 65.6 | 18.5 | 1.5 | 0.5 | 0.0 | 0.2 | 0.3 | 0.5 | 7.2 | 5.6 | 1.9 |
| P246L | 7.0 | 0.9 | 0.8 | 6.0 | 3.8 | 5.8 | 31.7 | 3.1 | 11.7 | 29.3 | 1.5 |
| P246S | 9.8 | 1.2 | 1.1 | 5.7 | 3.7 | 5.6 | 33.2 | 3.0 | 9.7 | 26.8 | 7.7 |
| S365I | 30.6 | 7.9 | 8.1 | 15.3 | 9.1 | 10.4 | 7.9 | 0.8 | 3.1 | 6.7 | 10.5 |
| S365L | 28.9 | 7.4 | 8.5 | 16.4 | 9.8 | 12.3 | 5.8 | 0.9 | 3.6 | 6.4 | 9.6 |
| V534F | 40.0 | 10.2 | 9.3 | 3.4 | 0.7 | 2.9 | 13.2 | 1.5 | 4.7 | 14.1 | 8.1 |
| Wild type LIP1 | 3.9 | 1.7 | 3.4 | 6.7 | 3.9 | 9.8 | 31.7 | 2.8 | 8.8 | 27.4 | 11.3 |
| Calf esterase | 37.1 | 11.2 | 3.8 | 7.5 | 4.2 | 7.5 | 12.9 | 1.7 | 4.1 | 10.0 | 12.6 |
| Lamb esterase | 45.5 | 16.4 | 4.5 | 7.7 | 3.8 | 4.4 | 7.6 | 0.5 | 3.6 | 5.9 | 14.4 |
| Kid esterase | 43.8 | 17.4 | 4.9 | 8.5 | 4.1 | 4.9 | 7.6 | 0.6 | 2.9 | 5.4 | 11.7 |

Example 7: Fatty Acid Specificity of LIP1 Variants Using on Butter Fat as Substrate Butter with fat content of approximately 80% (w/w) was melted in a 40° C. water bath. The liquid butter was mixed with 1% triton X-100 solution in a ratio of 1:10 (v/v). The pH was adjusted to 5.5 by adding 0.1 M HCl solution. A mixture of 800 μL butter fat emulsion and 100 μL of a suitable dilution of a supernatant of shake flask grown LIP1 variant, wild type LIP1 or reference sample was incubated overnight (approximately 16 h) in a 37° C. water bath with continuous mixing. A suitable dilution of the enzyme is the amount of enzyme that realizes a degree of hydrolysis of at least 1 mol % but not more than 50 mol %. After stopping the reaction by adding 100 μL 1 M HCl, the free fatty acid content was determined with gas chromatography (see Example 9).

Table 5 shows the fatty acid specificity of LIP1 mutant lipase with a mutation F345L, L307W, L410W, P246A, P246F, P246L, P246S, S365I, S365L, or V534F and the wild type LIP1 lipase on butter fat as substrate. As a reference the specificity of three commercial lipases from animal origin (Kerry kid lipase (DSM batch GT00013178), Kerry Halal calf lipase (DSM batch GT00012987) and Kerry lamb lipase (DSM batch GT00012631) were measured in the same way as described above. When comparing with LIP1 wild type, the specificity towards short chain fatty acids (C4:0 and C6:0) was significantly improved for variant F345L, L307W, L410W, P246F, S365I, S365L and V534F. For these improved variants, the fatty acid profiles are comparable with the profiles of the commercial animal lipases that are currently in use for cheese application.

TABLE 5

Free fatty acid profiles (as mol %) of LIP1 variants and reference samples after overnight incubation in butter fat/triton X-100 emulsion at 37° C. and pH 5.5. Last column gives the total amount of free fatty acids formed in mmol/kg.

| Variant | FFA formed in butter/triton X-100 emulsion (mol % FFA) | | | | | | | | | | Total FFA (mmol/kg) |
|---|---|---|---|---|---|---|---|---|---|---|---|
| | C4:0 FFA | C6:0 FFA | C8:0 FFA | C10:0 FFA | C12:0 FFA | C14:0 FFA | C16:0 FFA | C16:1 FFA | C18:0 FFA | C18:1 FFA | |
| F345L | 42.4 | 19.2 | 10.3 | 12.3 | 1.7 | 2.0 | 5.8 | 0.5 | 0.0 | 5.8 | 2.1 |
| L307W | 68.8 | 14.9 | 4.0 | 2.6 | 1.0 | 2.2 | 6.5 | 0.0 | 0.0 | 0.0 | 0.9 |
| L410W | 27.6 | 8.4 | 8.5 | 19.9 | 8.3 | 14.2 | 9.2 | 0.6 | 1.4 | 2.0 | 7.1 |
| P246A | 7.8 | 1.2 | 0.8 | 5.7 | 4.1 | 9.2 | 36.8 | 2.8 | 8.0 | 23.6 | 7.7 |
| P246F | 73.8 | 22.0 | 2.7 | 1.1 | 0.3 | 0.1 | 0.0 | 0.0 | 0.0 | 0.0 | 1.1 |
| P246L | 4.8 | 0.1 | 0.4 | 6.1 | 4.6 | 8.2 | 41.8 | 2.6 | 4.2 | 27.2 | 1.1 |
| P246S | 7.5 | 1.7 | 1.6 | 6.6 | 4.2 | 9.8 | 36.6 | 1.6 | 8.8 | 21.6 | 6.9 |
| S365I | 27.4 | 8.2 | 6.4 | 11.6 | 8.2 | 13.3 | 14.8 | 1.0 | 1.1 | 8.1 | 9.1 |
| S365L | 23.8 | 8.8 | 7.3 | 14.4 | 10.0 | 18.6 | 9.2 | 1.4 | 0.9 | 5.5 | 9.4 |
| V534F | 30.2 | 10.3 | 8.9 | 6.0 | 1.2 | 5.1 | 20.0 | 1.8 | 1.6 | 15.0 | 6.0 |
| Wild type LIP1 | 3.8 | 1.9 | 3.7 | 7.2 | 4.1 | 12.3 | 35.5 | 2.6 | 7.3 | 21.6 | 12.4 |
| Calf esterase | 25.8 | 10.2 | 4.3 | 8.6 | 4.8 | 11.5 | 19.7 | 1.5 | 2.5 | 11.3 | 8.2 |
| Lamb esterase | 36.5 | 14.4 | 4.6 | 8.5 | 4.8 | 7.8 | 12.7 | 0.8 | 3.0 | 7.0 | 8.0 |
| Kid esterase | 34.2 | 15.0 | 5.5 | 10.7 | 5.6 | 8.7 | 11.9 | 1.0 | 1.6 | 5.7 | 6.0 |

Example 8: Fatty Acid Specificity on Processed Cheese

Processed cheese (ERU Goudkuipje NatureI) was liquified by heating for 2 hours at 50° C. Subsequently 1 mL of a suitable dilution of a supernatant of shake flask grown LIP1 variant, wild type LIP1 or reference sample was added to 20 g liquified processed cheese. A suitable dilution of the enzyme is the amount of enzyme that realizes a degree of hydrolysis of at least 1% but not more than 50%. After thorough mixing the closed reaction tubes were incubated in a hybridization oven (Techne® Hybridiser HB-1D) at 20 rpm for 70 hours at 40° C. The reaction was stopped by heating the tubes for 30 minutes at 85° C. The free fatty acid content was determined with gas chromatography (see Example 9).

Table 6 shows the fatty acid specificity of Lip1 mutant lipase with a mutation F345L, L307W, P246A, P246L, P246S, S365I or V534F and the wild type Lip1 lipase on processed cheese as substrate. As a reference the specificity of three commercial lipases from animal origin (Kerry kid lipase (DSM batch GT00013178), Kerry Halal calf lipase (DSM batch GT00012987) and Kerry lamb lipase (DSM batch GT00012631) were measured in the same way as described above. When comparing with LIP1 wild type, the specificity towards short chain fatty acids (C4:0 and C6:0) was significantly improved for variant F345L, L307W, V534F and to lesser extent also S365I. For these improved variants, the fatty acid profiles are comparable with the profiles of the commercial animal lipases that are currently in use for cheese application.

TABLE 6

Free fatty acid profiles (as mol %) of LIP1 variants and reference samples after 70 h incubation in processed cheese at 40° C. Last column gives the total amount of free fatty acids formed in mmol/kg.

| Variant | FFA formed in processed cheese (mol % FFA) | | | | | | | | | | | Total FFA (mmol/kg) |
|---|---|---|---|---|---|---|---|---|---|---|---|---|
| | C4:0 FFA | C6:0 FFA | C8:0 FFA | C10:0 FFA | C12:0 FFA | C14:0 FFA | C16:0 FFA | C16:1 FFA | C18:0 FFA | C18:1 FFA | C18:2 FFA | |
| F345L | 41.8 | 19.7 | 10.8 | 7.9 | 1.4 | 1.6 | 4.4 | 0.0 | 2.0 | 8.4 | 1.9 | 32 |
| L307W | 53.0 | 7.9 | 2.7 | 1.4 | 0.8 | 2.9 | 10.4 | 0.2 | 4.2 | 10.3 | 6.2 | 23 |
| P246A | 15.2 | 3.0 | 0.9 | 4.0 | 4.6 | 7.0 | 28.3 | 2.4 | 8.3 | 25.9 | 0.4 | 347 |
| P246L | 21.0 | 4.4 | 2.1 | 4.9 | 5.5 | 6.4 | 25.7 | 2.1 | 5.2 | 20.9 | 1.7 | 94 |
| P246S | 15.2 | 3.0 | 1.3 | 4.7 | 5.3 | 5.1 | 30.0 | 2.3 | 6.8 | 23.9 | 2.3 | 66 |
| S365I | 22.7 | 5.2 | 12.6 | 18.5 | 20.2 | 7.7 | 3.6 | 0.0 | 3.1 | 5.2 | 1.2 | 22 |
| V534F | 45.4 | 12.1 | 17.3 | 2.3 | 0.5 | 2.1 | 8.0 | 0.9 | 2.2 | 8.4 | 0.9 | 35 |
| Wild type LIP1 | 9.6 | 1.8 | 2.7 | 5.1 | 5.7 | 8.7 | 29.1 | 3.9 | 5.0 | 26.6 | 1.8 | 121 |
| Calf esterase | 32.0 | 11.3 | 3.7 | 6.6 | 6.7 | 10.3 | 13.4 | 1.5 | 4.3 | 9.3 | 1.0 | 94 |
| Lamb esterase | 42.6 | 18.3 | 5.2 | 7.8 | 6.1 | 5.6 | 6.0 | 0.5 | 2.7 | 5.0 | 0.3 | 110 |
| Kid Lipase | 39.6 | 16.7 | 4.5 | 7.7 | 6.0 | 5.9 | 7.7 | 0.6 | 4.0 | 7.1 | 0.3 | 93 |

Example 9: Determination of Free Fatty Acids Via Gas Chromatography

9.1 Sample Preparation 100 mg of the sample was weighed and mixed with 2.0 ml distilled water and mixed to a homogenous blend. To this blend 100.0 µL 4 N HCl; and 5.0 mL chloroform; and 1.00 mL internal standard solution containing valeric acid (FA C5), tridecanoic acid (FA C13) and heptanoic acid (FA 017) solved (in chloroform) at a level of 5 mg/L were added. The whole mixture was stirred overnight (>16 hr) at 30° C. using a stirring plate. After centrifugation (14000 rpm), 1 µl of the chloroform layer was directly injected into the GC for free fatty acid analyses.

9.2 Equipment Parameters

The fatty acid analyses were carried out on an Agilent 7890 gas chromatograph with backflush using a FFAP column (Agilent FFAP/HP) of 30 m×0.25 mm with a film thickness of 250 µm coupled to an Optic PTV injector (GL sciences) and a FID detector (FID kept constant at 325° C.). After the sample injection, oven temperature was kept at 40° C. for 2.5 min, then heated up at 10° C./min until 240° C. and kept at this temperature for 2.5 min. The PTV injector was kept at 50° C. for 5 s, then heated up at 10° C./s until 200° C. for 95 s and then heated up at 60° C./s until 500° C. for 1020 s.

The column flow was set to 6 mL/min with hydrogen as carrier gas. The fatty acid analysis used a split flow of 50 mL/min. The backflush used a flow of 0.5 mL/min for 1 min and then increased to 8 mL/min with a rate of 100 mL/min. The sample was injected using a CombiPal XYZ robotic auto sampler at a speed of 50 µl/sec.

The fatty acids numbers were calculated using the internal standards, the FA C4 to C8 using internal standard C5; FA C10 to C14 using internal standard C13 and FA C16 to C20 using internal standard C17.

---

The invention claimed is:

1. A polypeptide having lipase activity wherein the polypeptide is
   a polypeptide, which, when aligned with the polypeptide according to SEQ ID NO: 1, comprises at least 80% identity to the amino acid sequence of SEQ ID NO: 1 and comprises at least one amino acid substitution resulting in Ser (S), Ala (A) or Leu (L) at position 246, Trp (W) at position 307, Leu (L) at position 345, Ile (I) at position 365, and/or Phe (F) at position 534, wherein the position is defined with reference to SEQ ID NO: 1, wherein Ala(A) at position 1 in SEQ ID NO: 1 is counted as number 1.

2. The polypeptide according to claim 1, wherein the polypeptide at least comprises one amino acid substitution resulting in Trp (W) at position 307, wherein Ala (A) at position 1 in SEQ ID NO: 1 is counted as number 1, wherein said polypeptide has at least 80% identity to amino acid sequence of SEQ ID NO: 1 and wherein said polypeptide has a higher specificity towards butyrate as a side chain than the specificity towards octanoate and/or palmitate as a side chain.

3. The polypeptide according to claim 1, wherein the polypeptide least comprises one amino acid substitution resulting in Leu (L) at position 345, wherein Ala (A) at position 1 in SEQ ID NO: 1 is counted as number 1, wherein said polypeptide has a higher specificity towards butyrate as a side chain than the specificity towards octanoate and/or palmitate as a side chain.

4. The polypeptide according to claim 1, wherein the polypeptide is a polypeptide of SEQ ID NO: 1 and at least comprises one amino acid substitution resulting in Phe (F) at position 534, wherein Ala (A) at position 1 in SEQ ID NO: 1 is counted as number 1, wherein said polypeptide has a higher specificity towards butyrate as a side chain than the specificity towards octanoate and/or palmitate as a side chain.

5. The polypeptide according to claim 1, wherein the polypeptide at least comprises one amino acid substitution resulting in Ile (I) at position 365, wherein Ala (A) at position 1 in SEQ ID NO: 1 is counted as number 1, wherein said polypeptide has a higher specificity towards butyrate as a side chain than the specificity towards octanoate and/or palmitate as a side chain.

6. The polypeptide according to claim 1 that is an isolated, pure, recombinant, or synthetic polypeptide.

7. The polypeptide according to claim 1, wherein the polypeptide having lipase activity has a higher specificity towards butyrate as a side chain than the specificity towards octanoate and/or palmitate as a side chain.

8. A composition comprising the polypeptide according to claim 1.

9. A method for generating a variant polypeptide having lipase activity wherein the method comprises
   a. selecting a parent polypeptide comprising at least 80% identity to the amino acid sequence according to SEQ ID NO: 1; and,
   b. substituting at least one amino acid into Ser (S), Ala (A) or Leu (L) at position 246, Trp (W) at position 307, Leu (L) at position 345, Ile (I) at position 365, and/or Phe (F) at position 534, wherein said position is defined with reference to SEQ ID NO: 1, wherein alanine at position 1 in SEQ ID NO: 1 is counted as number 1; and
   c. generating the variant polypeptide, wherein the polypeptide having lipase activity has a higher specificity towards butyrate than the specificity towards octanoate and/or palmitate.

10. A nucleic acid encoding a lipase, which has at least 80% sequence identity to SEQ ID NO: 2, wherein SEQ ID NO: 2 comprises at least one mutation resulting in Ser (S), Ala (A) or Leu (L) at position 246, Trp (W) at position 307, Leu (L) at position 345, Ile (I) at position 365, and/or Phe (F) at position 534 of the amino acid sequence of SEQ ID NO: 1, wherein the position is defined with reference to SEQ ID NO: 1, wherein alanine at position 1 in SEQ ID NO: 1 is counted as number 1.

11. An expression vector comprising a nucleic acid according to claim 10 operably linked to at least one control sequence that directs expression of the polypeptide in a host cell.

12. A recombinant host cell comprising a nucleic acid according to claim 10, or an expression vector comprising said nucleic acid.

13. A method for preparing a polypeptide according to claim 1, comprising cultivating a host cell in a suitable fermentation medium, under conditions that allow expression of the polypeptide, and optionally recovering the polypeptide.

14. A process for preparing a product comprising a lipid comprising bringing the lipid into contact with a polypeptide according to claim 1.

15. The polypeptide according to claim 1, for improving flavour in a product comprising a lipid.

16. The polypeptide according to claim 15, wherein improving flavour comprises reducing the formation of fatty acids having at least 8 carbon atoms, as compared to the use of a polypeptide comprising an amino acid sequence according to SEQ ID NO: 1.

17. The process according to claim 14, wherein the product comprising a lipid is a food product, optionally a dairy product, optionally butter, cream or cheese.

18. The polypeptide of claim 15, wherein the product comprising a lipid is a food product, optionally a dairy product, optionally butter, cream or cheese.

19. The process for preparing a product comprising a lipid comprising bringing the lipid into contact with a composition according to claim 8.

20. The polypeptide of claim 1, wherein the polypeptide is encoded by a nucleic acid which has at least 80% identity to the nucleotide sequence of SEQ ID NO: 2, wherein SEQ ID NO: 2 comprises at least one mutation resulting in an amino acid Ser (S), Ala (A) or Leu (L) at position 246, Trp (W) at position 307, Leu (L) at position 345, Ile (I) at position 365, and/or Phe (F) at position 534 of a polypeptide according to SEQ ID NO: 1, wherein Ala (A) at position 1 in SEQ ID NO: 1 is counted as number 1.

21. The polypeptide of claim 1, which, when aligned with the polypeptide according to SEQ ID NO: 1, consists of a polypeptide at least 80% identity to the amino acid sequence of SEQ ID NO: 1 and comprises at least one amino acid substitution resulting in Ser (S), Ala (A) or Leu (L) at position 246, Trp (W) at position 307, Leu (L) at-position 345, Ile (I) at position 365, and/or Phe (F) at position 534, wherein the position is defined with reference to SEQ ID NO: 1, wherein Ala(A) at position 1 in SEQ ID NO: 1 is counted as number 1.

* * * * *